United States Patent
LaBarge et al.

(10) Patent No.: US 11,407,968 B2
(45) Date of Patent: Aug. 9, 2022

(54) SYSTEMS, METHODS, AND APPARATUSES FOR MEDIA REHYDRATION

(71) Applicant: LIFE TECHNOLOGIES CORPORATION, Carlsbad, CA (US)

(72) Inventors: Shawn LaBarge, Clarence Center, NY (US); Rebecca Moore, Orchard Park, NY (US); Daniel Alessi, West Seneca, NY (US); Richard Hassett, Tonawanda, NY (US); Peter Rezac, Berlin, MA (US); Karsten Nielsen, Lexington, MA (US); Neal Anderson, Windham, NH (US); Tom Donze, San Bruno, CA (US); Elizabeth Clark, Harvard, MA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 15/120,158

(22) PCT Filed: Jan. 29, 2015

(86) PCT No.: PCT/US2015/013481
§ 371 (c)(1),
(2) Date: Aug. 19, 2016

(87) PCT Pub. No.: WO2015/126589
PCT Pub. Date: Aug. 27, 2015

(65) Prior Publication Data
US 2017/0058244 A1   Mar. 2, 2017

Related U.S. Application Data

(60) Provisional application No. 61/943,107, filed on Feb. 21, 2014.

(51) Int. Cl.
*C12M 1/00* (2006.01)
*C12M 1/36* (2006.01)

(52) U.S. Cl.
CPC ............ *C12M 23/28* (2013.01); *C12M 23/26* (2013.01); *C12M 23/40* (2013.01); *C12M 23/52* (2013.01);
(Continued)

(58) Field of Classification Search
CPC ...... C12M 29/06; C12M 29/20; C12M 41/48; C12M 99/00; C12M 23/26; C12M 23/28;
(Continued)

(56) References Cited

U.S. PATENT DOCUMENTS

2003/0043688 A1 * 3/2003 Peterson ............... B01F 1/0016
366/137
2004/0087022 A1   5/2004 Fike et al.
(Continued)

FOREIGN PATENT DOCUMENTS

JP   S53-16961    2/1978
JP   03-039087 A  2/1991
(Continued)

OTHER PUBLICATIONS

Kelly, J., "Comparison of Disposable Mixing Systems Using AGT for Preparation of Large Volumes of Media", *IBC's 4th International Single-Use Bioprocess Systems and Applications*, http://www.lifetechnologies.com/content/dam/LifeTech/migration/en/filelibrary/bioproduction/pdfs.par.33405.file.dat/agt-disposable mixing systems.pdf, Apr. 13, 2011, 30 Pages.
(Continued)

*Primary Examiner* — Lydia Edwards
(74) *Attorney, Agent, or Firm* — Workman Nydegger

(57) ABSTRACT

The present set of embodiments relate to a system, method, and apparatus for hydrating and mixing a liquid medium
(Continued)

from a dry medium. Such systems, methods, and apparatuses can be used in the biotech industry because they can be used to provide prepackaged dry media in a format that can be quickly rehydrated free of issues with operator error found in more conventional media rehydration systems using mixing tanks and reactors.

9 Claims, 20 Drawing Sheets

(52) U.S. Cl.
CPC ............ *C12M 29/04* (2013.01); *C12M 29/06* (2013.01); *C12M 29/20* (2013.01); *C12M 29/26* (2013.01); *C12M 41/48* (2013.01); *C12M 99/00* (2013.01)

(58) Field of Classification Search
CPC ...... C12M 23/40; C12M 23/52; C12M 29/04; C12M 29/26; C12M 37/02; C12M 41/30; C12M 41/40
See application file for complete search history.

(56) References Cited

U.S. PATENT DOCUMENTS

| | | | | |
|---|---|---|---|---|
| 2005/0173003 | A1* | 8/2005 | Laverdiere | G05D 16/2013 137/487.5 |
| 2010/0080077 | A1* | 4/2010 | Coy | B01F 5/02 366/137 |
| 2010/0193433 | A1* | 8/2010 | Hausin | C02F 3/06 210/620 |
| 2011/0013474 | A1 | 1/2011 | Ludwig et al. | |
| 2014/0349385 | A1* | 11/2014 | Erdenberger | B01F 15/00714 435/302.1 |

FOREIGN PATENT DOCUMENTS

| | | |
|---|---|---|
| JP | 2013500207 | 1/2013 |
| RU | 2005354 | 1/1994 |
| WO | 2009/153790 | 6/2009 |
| WO | 2013/040161 | 3/2013 |

OTHER PUBLICATIONS

PCT/US2015/013481, International Search Report and Written Opinion dated Jun. 29, 2015, 13 Pages.

Wernli, U. et al., "CD 293 AGT medium for the cultivation of HEK293 EBNA cells in small-scale bioreactors: an application report", *Quest*, vol. 5, No. 1, Aug. 1, 2008, 18-21.

Xcellerex, Inc., "XDUO Quad Intelligent Single-Use Mixing System", 2012, 2 Pages.

Quest International, Bioproduct, "CD 293 AGT(TM) medium for the cultivation of HEK 293 EBNA cells in small-scale bioreactors: an application report", *QUEST* [online], vol. 5 URL:http://www.researchgate.net/publication/267678679_CD_293_AGT_medium_for_the_cultivat_ion_of_HEK_293_EBNA_cells_in_small-scale_bioreactors_an_application_report, Aug. 2008, 18-21.

Japanese Office Action from JP2016-553324, dated Jan. 30, 2019.

* cited by examiner

SYSTEMS, METHODS, AND APPARATUSES FOR MEDIA REHYDRATION

CROSS-REFERENCE TO RELATED APPLICATIONS

This application is a 371 of International application no. PCT/US2015/013481, filed Jan. 29, 2015, and claims priority to U.S. application No. 61/943,107, filed Feb. 21, 2014, which disclosures are herein incorporated by reference in their entirety.

FIELD

The present disclosure generally relates to media rehydration systems and more particularly to systems, apparatuses and/or methods for hydrating and mixing a liquid medium from a dry medium.

BACKGROUND

Cell culture media are complex mixtures of synthetic and natural biological components that provide nutrients for cell propagation. It is typically prepared by thoroughly mixing in dry or dehydrated bulk storage forms (e.g., powders, granules, etc.) of cell culture media with a suitable solvent (e.g., sterile water, buffers, etc.) in a mixing container to produce a liquid cell culture media. Mixing systems can generally be categorized into two main types; reusable and single use mixing systems.

Reusable mixing systems generally consists of a fixed rigid tank (useful for larger volumes), or a mobile rigid tank (for smaller volumes) with a mixing impeller mounted to a driveshaft and motor. The dry media is weighed by an operator to a specified weight for the volume of media being prepared. The operator fills the tank with water to the appropriate level, adds the dry media, and turns on the mixer for a specified period of time (generally 30-60 min.) until the mixing (hydration) of the media is complete. After the media is mixed, it is pumped through a filter (to remove contaminants) into a sterile bioreactor or sterile holding vessel. Once the tank has been emptied, the tank along with the mixing device must be cleaned using a validated cleaning protocol which sometimes requires the use of caustic solutions. Therefore, this type of system is not designed as a "plug and go" system as it requires a lot of initial preparation and post cleaning by the operator.

Single use mixing systems generally consist of a fixed piece of hardware containing a drive motor, computer, and a rigid shell which houses a single use mixing bag or liner. The dry media and water are prepared in the same manner as above. However, prior to the water filling the mixing bag/liner, the bag/liner must be placed properly into the rigid shell and affixed to the drive motor. Once the bag has been put in place and filled with water and dry media, the drive motor is started which starts the mixing cycle. The mixing cycle is run for a period of time (generally 30-60 min.) until the mixing is complete. Upon completion of mixing the media is pumped through a filter into a sterile bioreactor or sterile holding vessel. Once the mixing bag/liner has been emptied, it is removed from the rigid shell and thrown away. However, until now, setting up more than one system (bag or capsule) was difficult and/or time consuming, and in some cases, could not be easily scaled up to produce higher volume batches. Also, operator measurement and handling of the bulk dry powder exposed the media to possible contamination, which sometimes caused the final rehydrated media to be discarded because of the stringent asepsis requirements for most cell production, biopharmaceuticals and research applications.

As such, there is a need for a convenient, single use mixing system that is cost effective, does not require the performance of several onerous system set-up steps at the front-end by the user, and which can be designed as a "plug and go" system. This provides increased flexibility and modularity during bioprocessing which can reduce capital equipment costs for customers.

BRIEF DESCRIPTION OF THE DRAWINGS

For a more complete understanding of the principles disclosed herein, and the advantages thereof, reference is now made to the following description taken in conjunction with the accompanying drawings, in which.

Figure 1:
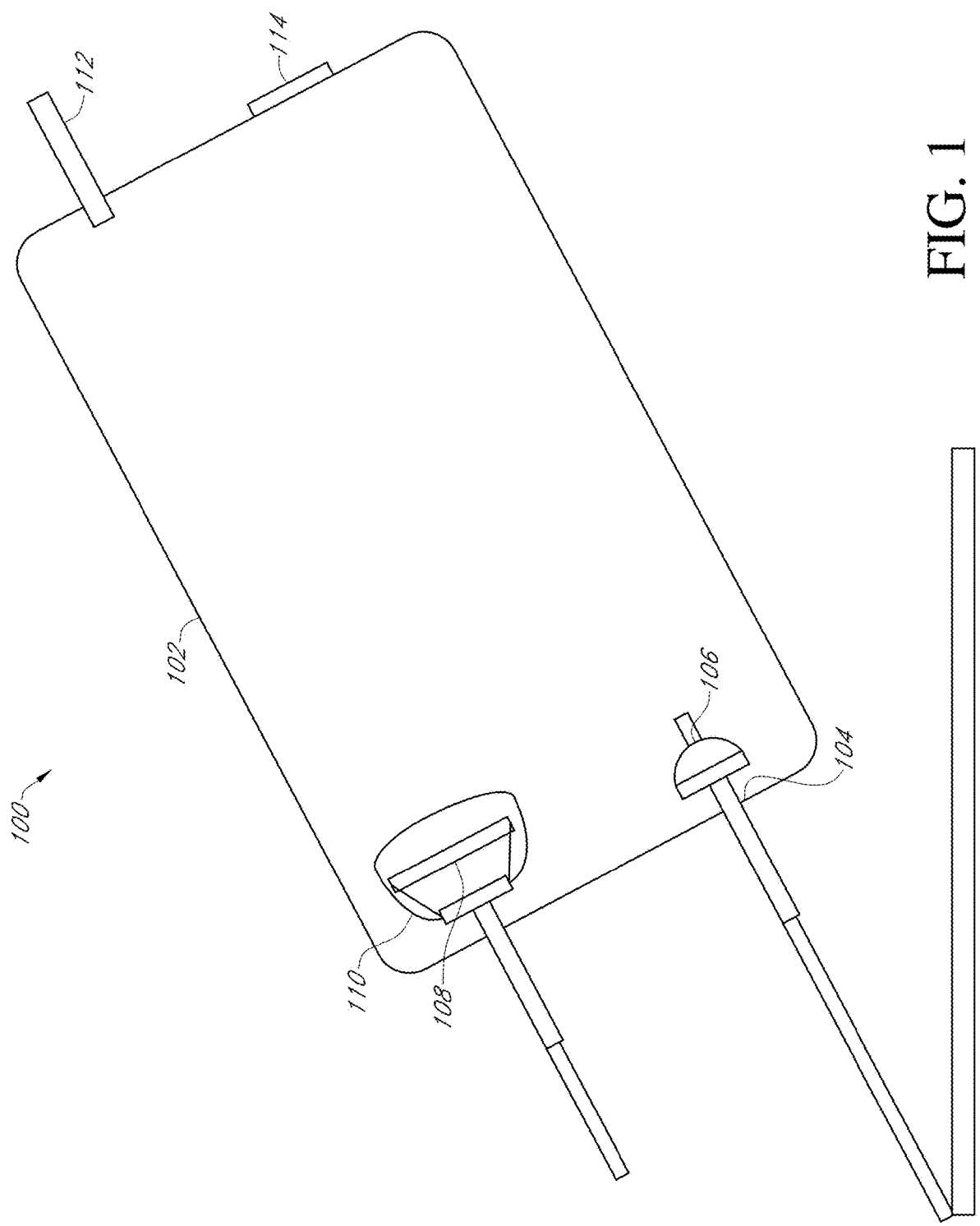
FIG. 1 is a schematic diagram of a media mixing vessel 100 for preparing liquid media from dry bulk storage forms (e.g., powders, granules, etc.) of media ('Dry Media'), in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Embodiments of systems, methods and apparatuses for hydrating, mixing and/or preparing a liquid medium from a dry medium are described in the accompanying description and figures.

In the figures, numerous specific details are set forth to provide a thorough understanding of certain embodiments. One skilled in the art will appreciate, however, that certain embodiments may be practiced without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of certain embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Furthermore, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

In order that the present disclosure may be more readily understood, certain terms are first defined. Additional definitions are set forth throughout the detailed description.

The term "dry powdered medium" or DPM, as used herein, refers to dry medium that is produced using various milling technologies, including, but not limited to: FITZ-MILL™, JET MILL™, pin mill, ball mill, cone mill, etc., with a particle size that falls within the range of 10 microns to 150 microns The term "advanced granulation technology" or AGT, as used in this application refers to a process of preparing cell culture medium that involves spraying one or more aqueous solutions onto air suspended powdered medium components, with gentle, rapid evaporation of water, under conditions where sensitive components do not lose their efficacy, resulting in an agglomerated granule and a homogenous distribution of the sprayed ingredients throughout the agglomerated granules. The granulated powder (AGT) is discussed in Fike et al., Cytotechnology, 2006, 36:33-39, and in Applicants' patents and/or patent applications: U.S. Pat. No. 6,383,810, issued May 7, 2002; U.S. Pat. No. 7,572,632, issued Aug. 11, 2009; and in U.S. patent application Ser. No. 11/669,827 filed Jan. 31, 2007, whose disclosures are hereby incorporated by reference in their entirety. Briefly, AGT media is a dry, powdered medium that is highly desired in the industry, for properties like large particle size, reduced amount of fine dust while handling, high wettability, low dissolution times into solvent, auto-pH and auto osmolarity maintenance, etc.

The term "susceptible compound" or "sensitive compound" or "labile compound" as used in this application refers to substance, chemical or compound to be protected from degradation or reaction with "reactive species" present in dry format media. Examples of such compounds in cell culture media include but are not limited to: ethanolamine, vitamins, cytokines, growth factors, hormones, etc.

The term "encapsulating agent" may sometimes be referred to as "sequestering agent" in this application, and refers to the encapsulation, protection, separation, or sequestering of susceptible chemicals or components in the cell culture medium or feed, away from conditions that enhance degradation, or reactivity with other reactive chemicals such as amino acids, trace metal elements such as manganese, copper, etc., inorganic buffers such as sodium bicarbonate and other sodium phosphates; and organic buffers such as MOPS, HEPES, PIPES, etc., which may react slowly with the susceptible compound, thereby making the labile component lose its desirable properties over time. Alternately, encapsulation, protection, separation, or sequestering may be done to protect the susceptible chemical or component from physical damage such as, radiation damage, or heat damage, or physical stress, from exposure to moisture/condensation, or from dehydration, etc. The terms "protect" or "separate" or "sequester" or "encapsulate" may have been used interchangeably in the disclosure, and convey the concept of protecting the susceptible chemical or compound from degrading conditions or chemicals. The "soluble sequestering agent" itself may be soluble upon reconstitution with an aqueous medium, whereupon it releases the "sensitive" encapsulated material. Or, the "insoluble sequestering agent" may be insoluble upon reconstitution with an aqueous medium, whereupon after releasing the "sensitive" encapsulated material, it can be removed by means such as filtration, decanting, etc. from the reconstituted end product.

Examples of matrices that may be used for microencapsulation include but are not limited to, alginate, poly-L-lactic acid (PLL), chitosan, agarose, gelatin, hyaluronic acid, chondroitin sulfate, dextran, dextran sulfate, heparin, heparin sulfate, heparin sulfate, gellan gum, xanthan gum, guar gum, water soluble cellulose derivatives, carrageenan and so on.

Optionally, the microcapsules may be coated for one of several reasons: to extend and slowly release the microcapsule components; for protection of labile components against any type of damage, say, radiation, heat, dehydration, etc. Coatings may include but are not limited to, poly-glycolic acid, PLGA (poly-lactic-co-glycolic acid), collagen, polyhydroxy-alkanoates (PHA), poly-ε-caprolactone, poly-ortho esters, poly-anhydrides, poly-phosphazenes, poly-amino acids, polydimethylsiloxane, polyurethanes, poly-tetrafluoroethylene, polyethylene, polysulphone, poly-methyl methacrylate, poly-2-hydroxyethylmethacrylate, polyamides, polypropylene, poly-vinyl chloride, polystyrene, poly-vinyl pyrrolidone, etc.

Labile media or feed components include, but are not limited to, compounds such as vitamins, for example, thiamine, B12; amino acids like glutamine; polyamines like ethanolamine; cytokines; growth factors, etc.

Agents used to chelate, deactivate or shut reactive molecules within media include, but are not limited to, compounds such as EDTA, citrate, succinate, cyclodextrin, clatharates, dendrimers, amino acids, etc.

The cell culture medium is preferably a powdered cell culture medium. In one embodiment, the powdered cell culture medium is an advanced granulation technology (AGT) cell culture medium. The cell culture media also refers to feeds, concentrated supplements, concentrated media, and in some instances, liquid media, as applicable.

The terms "cell culture" or "culture" as used in this application refer to the maintenance of cells in an artificial (e.g., an in vitro) environment. It is to be understood, however, that the term "cell culture" is a generic term and may be used to encompass the cultivation not only of individual prokaryotic (e.g., bacterial) or eukaryotic (e.g., animal, plant and fungal) cells, but also of tissues, organs, organ systems or whole organisms, for which the terms "tissue culture," "organ culture," "organ system culture" or "organotypic culture" may occasionally be used interchangeably with the term "cell culture."

The term "cultivation" as used in this application refers to the maintenance of cells in an artificial environment under conditions favoring growth, differentiation, or continued viability, in an active or quiescent state, of the cells. Thus, "cultivation" may be used interchangeably with "cell culture" or any of its synonyms described above.

The terms, "cell culture medium," "culture medium," or "medium" (and in each case plural media) as used in this application refer to a nutritive composition that supports the cultivation and/or growth of cells. The cell culture medium may be a complete formulation, i.e., a cell culture medium that requires no supplementation to culture cells, may be an incomplete formulation, i.e., a cell culture medium that requires supplementation or may be a medium that may supplement an incomplete formulation or in the case of a complete formulation, may improve culture or culture results. The terms "cell culture medium," "culture medium," or "medium" (and in each case plural media) refer to unconditioned cell culture media that has not been incubated with cells, unless indicated otherwise from the context. As such, the terms "cell culture medium," "culture medium," or "medium" (and in each case plural media) are distinguished from "spent" or "conditioned" medium, which may contain many of the original components of the medium, as well as a variety of cellular metabolites and secreted proteins.

The term "powder" or "powdered" as used in this application refers to a composition that is present in granular form, which may or may not be complexed or agglomerated with a solvent such as water or serum. The term "dry powder" may be used interchangeably with the term "powder;" however, "dry powder" as used herein simply refers to the gross appearance of the granulated material and is not intended to mean that the material is completely free of complexed or agglomerated solvent unless otherwise indicated.

The terms, "flexible bag," "flexible portion," or "flexible liner" as used in this application refers to a container that can holds media (dry or liquid forms). The bag may include one or more layer(s) of flexible or semi-flexible water and/or chemical resistant material depending on size, strength and volume requirements. The inside surface of the bag may be smooth and provide a substantially sterile environment (e.g. for media production, culturing cells or other organisms, for food production, etc.). The bag may include one or more openings, pouches (e.g., for inserting one or more probes, devices, etc.) or the like. Furthermore, the bag can provide a disposable alternative to a solid vessel in a conventional reusable mixing tank. The flexible bag may further include a bearing and seals or o-rings, and may be entirely disposable.

A "1× formulation" refers to any aqueous solution that contains some or all ingredients found in a cell culture medium at working concentrations. The "1× formulation" can refer to, for example, the cell culture medium or to any subgroup of ingredients for that medium. The concentration of an ingredient in a 1× solution is about the same as the concentration of that ingredient found in a cell culture formulation used for maintaining or cultivating cells in vitro. A cell culture medium used for the in vitro cultivation of cells is a 1× formulation by definition. When a number of ingredients are present, each ingredient in a 1× formulation has a concentration about equal to the concentration of those ingredients in a cell culture medium. A "1× formulation" of these amino acids contains about the same concentrations of these ingredients in solution. Thus, when referring to a "1× formulation," it is intended that each ingredient in solution has the same or about the same concentration as that found in the cell culture medium being described. The concentrations of ingredients in a 1× formulation of cell culture medium are well known to those of ordinary skill in the art. See Cell Culture Technology for Pharmaceutical and Cell-Based Therapies, 42-50 (Sadettin Ozturk and Wei-Shou Hu eds., Taylor and Francis Group 2006), which is incorporated by reference herein in its entirety. The osmolarity and/or pH, however, may differ in a 1× formulation compared to the culture medium, particularly when fewer ingredients are contained in the 1× formulation.

In various embodiments, microsuspensions and dried microcapsule beads are disclosed where the concentration of the same ingredient is increased in the micro/nanosuspension, and is concentrated even further in a dry encapsulated bead format. Accordingly, a "7× formulation" is meant to refer to a concentration wherein each ingredient in that micro/nanosuspension or encapsulated bead is about 7 times more concentrated than the same ingredient in the corresponding liquid cell culture medium/feed or supplement. A "10× formulation" is meant to refer to a concentration wherein each ingredient in that micro/nanosuspension or encapsulated bead is about 10 times more concentrated than the same ingredient in the liquid cell culture medium/feed or supplement. As will be readily apparent, "5× formulation," "25× formulation," "50× formulation," "100× formulation," "500× formulation," and "1000× formulation" designate formulations that contain ingredients at about 5 to 25-, 25-50-, 50-70-, 70-100-, 100-500-, 500-1000-fold concentrations, respectively, as compared to a 1× cell liquid medium, feed or supplement. Again, the osmolarity and pH of the media formulation and concentrated solution may vary. A formulation may contain components or ingredients at 1× with respect to a particular cell culture protocol, but at a concentration, for example, 2, 2.5, 5, 6.7, 9, 12, etc.× with respect to a different culture protocol or different base medium.

Microsuspensions

Nutrient feeds, functional additives or supplements are generally provided as clear liquid concentrates or as powders that get reconstituted into dilute clear liquid concentrates for delivery directly into the bioreactor. This means that the components therein are never beyond their solubility limits. If they are prepared beyond their solubility limits, it is well known that precipitate forms, either as flakes or fine precipitates, usually white cloudiness in the bottle. Settling of these components occur in several hours, which means that the concentrated solution cannot be used to deliver accurate amounts of feed.

The media, feed and supplement compositions described in this disclosure have several desirable properties, which include but are not limited to, (i) ability to deliver certain components at "superconcentrated" levels extending far beyond their normal solubility limits in a culture system, (ii) increased ability to maintain media/feed functionality even after radiation sterilization, (iii) increased ability for extended release of internal components, (iv) high and quick solubility, (v) longer shelf life in dry format, (vi) increased thermostability, (vii) reduced risk of viral contamination up to 8 logs, (viii) the ability to be combined with other sterilizing technologies such as UV, filtration, and/or HTST pasteurization, (ix) the ability to be applied to a variety of dry media formats such as AGT, APM and DPM, as well as, to formulations having labile components at higher concentrations, (x) the ability to be applied to a variety of product types such as media, feeds, supplements, functional additives, etc. Due to these characteristics, the compositions can be added directly into a bioreactor or into a culture already in progress, and thereby can improve customer workflows and bioreactor productivity.

Accordingly, the compositions described in this disclosure are directed, in part, to cell culture media, concentrated feeds, functional additives, supplements that comprise a microsuspension; may also be directed to a novel cell culture media, feed and/or supplement composition comprising one or more encapsulated micro and/or nanosuspensions; and may further be directed to sterilized compositions that have been prepared using radiation such that the functionality of the media/feed is maintained even after exposure to radiation. Throughout this disclosure, some references may be made to cell culture media alone, but it would also include feeds and/or supplements, as applicable.

A micro/nanosuspension is a micron/nano-sized solid in an aqueous solvent base that, in one embodiment, does not separate over time. Micro/nanosuspensions, for example, provide a means of concentrating one or more media/feed components beyond the solubility limit of that component. Some desirable properties of micro/nanosuspensions include, but are not limited to, enabling increased nutrient supplement concentrations (e.g., amino acids) in minimal volume; extremely rapid dissolution of micro/nanosuspensions components in aqueous solutions (more rapid than the media would dissolve absent such preparation); capacity for encapsulation (i.e. for sterilization and protection of components in encapsulated form); capacity for direct addition of sterile, micro/nanosuspensions beads into pre-existing cultures in a bioreactor; the ability to increase efficiency and manufacturing processes in a bioreactor.

The micro/nanosuspension compositions described above may be useful in many applications, for example, in nutrient supplementation to significantly boost component concentrations beyond the level of solubility of the component in question, such that, volume of addition to the reactor is minimal; or, for encapsulating the microsuspensions, as described below, and making a dried form of the encapsulated bead resulting in a "super concentrated" supplement that can be directly added to the bioreactor, which has not been done before.

In various embodiments, microsuspensions can be made from any form of dry powder, of any component that needs to be provided in culture in a concentrated form, and provide at least a 2 to 5-fold, 5 to 10-fold, 10 to 15-fold, 15 to 20-fold, 20 to 25-fold, 25 to 30-fold, 30 to 50-fold, 50 to 70-fold, 70 to 100-fold concentration of the component in the microsuspension over an equivalent liquid concentrate or feed having the same component in solution.

Microencapsulation

This disclosure also provides microencapsulated forms of the micro/nanosuspension described above, that were made from a dry powdered cell culture medium, feed, supplement or concentrate. The resulting encapsulated products may be referred to as 'microcapsules', 'encapsulated bead', 'beads', 'capsules' or 'microbeads' in this disclosure. When the encapsulated micro/nanosuspension is dried into beads, the drying step provides a greater degree of concentration of the encapsulated micro/nanosuspensions. Microencapsulation may be done, for example, to "keep apart" or sequester sensitive or labile components in a complex mixture such as cell culture media/feed. Thus, encapsulation may yield higher concentrations of certain feed components such as, for example, amino acids, so that these feeds can be directly added as concentrated, high nutrient supplements into any culture system, for example, in fed-batch cultures. Further coating of the capsule may affect delayed-release of nutrients to into cell cultures (discussed below). Encapsulation can be done by: (a) a standard microencapsulation process of microsuspensions and nanosuspensions for "gently-releasing" some or all components over several hours; (b) an alternative bead-gelling process to significantly retard the internal component release.

In various embodiments, the agent used to encapsulate or embed the labile component was alginate. Alginate microcapsules have been used for many purposes, including drug delivery and the immobilization of cells growing in cell culture to enhance cell growth and viability. See e.g., Serp et al., Biotechnology and Bioengineering, 2000, 70(1):41-53; Breguet et. al., Cytotechnology, 2007, 53:81-93; Chayosumrit et al., Biomaterials, 2010, 31:505-14; U.S. Pat. Nos. 7,482,152; and 7,740,861, all of which are incorporated by reference in their entirety.

The encapsulation technique was also described in Applicants' co-pending application, PCT/US2012/024194, which described entrapping certain labile, sensitive or susceptible compounds such as ethanolamine, vitamins, growth factors like insulin, etc. in capsular materials, including but not limited to, alginate.

Without intending to be bound by any theory, it appears that encapsulating or embedding sensitive components within another molecule reduces the labile compound's direct contact with other components or conditions that promote its degradation, or reduces its stability. Methods describing the preparation of microcapsules for the reduction of ethanolamine degradation by microencapsulation is described in Applicant's co-pending application, PCT/US2012/024194, filed Feb. 7, 2012, whose disclosure is incorporated by reference herein in its entirety. Although those methods were primarily exemplified within the context of ethanolamine stabilization, they can be used/adapted to stabilize any susceptible or labile chemical or compound in a media, feed or supplement. It is understood that the microencapsulation methods described therein can be used for stabilizing any susceptible compound required for cell culture, including but not limited to, vitamins like thiamine, B12, etc., unstable amino acids such as glutamine, cytokines, growth factors, sensitive and valuable proteins or peptides, etc. and for enhanced delivery of the stabilized compound, and can be applied to fields beyond cell culture media development. In this disclosure, the encapsulation technique was adapted to micro/nanosuspension beads, which required adaptation of several steps and techniques. For instance, the entrapping steps for susceptible compounds in the PCT/US2012/024194 application lacked several steps. For encapsulation of microsuspensions, the capsular material, such as alginate, was mixed and blended with the microsuspension. This mix was then aspirated into a dispensing device such as a pipette or a dropper and droplets of encapsulated microsuspension were gradually generated by dropping the mix gently onto a non-stick surface, for example, on parafilm. Then, a cross-linking agent was added to the drop to form beads. These beads were desiccated and vacuum dried to remove moisture, and are generally referred to as "encapsulated microsuspension beads" or just "beads".

As one of skill in the art would know based on the instant disclosure, a variety of capsular materials may be used, or a variety of drop delivery devices including pipettes, droppers, syringes or any adaptation thereof may be used, or any cross-linking agent may be used, or the bead may be dried or desiccated by a variety of means and to differing degrees of dryness and/or hardness to encapsulate microsuspensions. One of skill in the art will be able to determine appropriate encapsulating agents for the purpose at hand, for instance, alginate, poly-L-lactic acid (PLL), chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives, carrageenan and so on.

Microcapsules are typically spherical particles having a diameter of 2 mm or less, usually within the diameter range of 0.05-1.5 mm. Typically, alginate microcapsules are formed by crosslinking between the polyanionic alginate and a divalent or trivalent polyvalent cation, such as calcium chloride. Other salts for cross-linking may be divalent or trivalent cations, such as magnesium chloride, barium chloride, and aluminum sulfate.

Encapsulation has several advantages, some of which include, but are not limited to, protection of labile components from degradation, or from unwanted reactions; or to delay and/or extend the release-time of the encapsulated components into cell culture In one embodiment, protection due to microencapsulation of media; or to increase the stability and storage of cell culture media, feeds and supplements comprising labile compounds at ambient temperatures. The encapsulated compound can be dried into beads, which can then be blended and/or mixed with other media components. Accordingly, micro/nanosuspensions may result in a 1-5%, 5-10%, 10-15%, 15-20%, 20-25%, 25-30%, 30-35%, 35-40%, 40-50%, 50-60%, 60-70%, 70-80%, 80-90%, or 90-100% reduction in any loss of media/labile component functionality, which may be measured by a suitable functional assay for the encapsulated labile or media component, using techniques known in the art, including the methods disclosed in this application. Examples of functional assays may be, the ability of a media/feed composition comprising microcapsules to increase the cell viability over days, or the cell number in a culture system, or recombinant protein production, or an increase in the amount and/or the function of a recombinant protein being expressed (for example, an enzyme or a receptor functional assay, or the stability of an encapsulated labile component like glutamine can be evaluated during culture, etc., as would be known to one of skill in the art).

In various embodiments, a sequestering agent like alginate can be used to encapsulate or embed an ethanolamine-dendrimer complex. Dendrimers are hyper-branched synthetic macromolecules that can be made using controlled sequential processes to give them defined structural and molecular weight characteristics; reviewed in Astruc et al., Chem. Rev. 2010, 110:1857-1959, which is hereby incorporated by reference in its entirety. Dendrimers can be used to prepare the encapsulated microsuspensions of the instant invention as well. In another embodiment, the dendrimer used in the methods as described in PCT/US2012/024194 was polyamidoamine, and it may be adapted for used in encapsulated micro/nanosuspensions. Other dendrimers that can be used in the methods described in this application include, but are not limited to polypropyleneimine (PPI) dendrimers, phosphorous dendrimers, polylysine dendrimers, polypropylamine (POPAM) dendrimers, polyethylenimine dendrimers, iptycene dendrimers, aliphatic poly (ether) dendrimers, or aromatic polyether dendrimers.

In various embodiments, microencapsulated micro/nano-suspensions can be made for any component that needs to be provided in culture in a concentrated form, and provides at least a 2 to 5-fold, 5 to 10-fold, 10 to 15-fold, 15 to 20-fold, 20 to 25-fold, 25 to 30-fold, 30 to 50-fold, 50 to 70-fold, 70 to 100-fold concentration of the component in the encapsulated micro/nanosuspension over an equivalent liquid concentrate or feed having the same component in solution. In one exemplary embodiment, the microsuspension preparation of a concentrated feed preparation as seen in the Figures was about 7-fold more concentrated than its corresponding liquid feed, whereas the dried encapsulated form of the same microsuspension was about 10-fold more concentrated than its corresponding liquid feed.

Advanced Granulation Technology (AGT)

Advanced Granulation Technology (AGT™) is a novel dry-form media format having significant advantages. Within a single granulated medium all components of a complex formulation are incorporated, to include buffers, growth factors, and trace elements. The resulting low dust, auto-pH formulation simply requires addition of water to yield a complete reconstituted 1× medium. Cyclodextrin technology as well as use of sodium salts and hydro-alcoholic solutions of lipids may be used in conjunction with the AGT process to deliver usable lipid in a dry medium format.

The agglomeration technology (e.g., AGT) can incorporate the use of fluid bed processors, such as for example, a Glatt GPCG Pro 120 Top Spraying Fluid Bed Processor which can be purchased from Glatt Pharmaceutical Services, Inc. Within this unit, dry powder medium components that have been previously dispensed, sized, and blended are transferred into the conical shaped product bowl of the fluid bed tower. As the fluid bed granulation process is initiated, this powder medium is transferred from the product bowl into the extended height of the fluid bed expansion chamber on a column of conditioned air.

The spraying of aqueous solutions of concentrated medium components onto a fluidized powder generates the granulation process. The previously prepared aqueous solutions are introduced high into the expansion chamber via a liquid pump skid and a pneumatically atomized nozzle. At this point in the chamber, the bed surface area is at its maximum resulting in a narrow particle size distribution of the final product. Once all the liquid solutions are delivered to the fluidized powder, the formed granules or agglomerates that are produced are subsequently dried with heated air until a final moisture setpoint for the material is achieved. As the final granules are sized and blended with any remaining temperature sensitive components, a complete and homogenous constituent medium is formed with the benefits of rapid dissolution, low dust generation, and auto-pH adjustment.

Throughout this application, the units "mesh" and "micron" are used to describe the size of dry media particles. Particle mesh size can be converted to units of microns using Table 1 below:

TABLE 1

Mesh to Micron Conversion Table

| MESH | MICRONS |
|---|---|
| 3 | 6730 |
| 4 | 4760 |
| 5 | 4000 |
| 6 | 3360 |
| 7 | 2830 |
| 8 | 2380 |
| 10 | 2000 |
| 12 | 1680 |
| 14 | 1410 |
| 16 | 1190 |
| 18 | 1000 |
| 20 | 841 |
| 25 | 707 |
| 30 | 595 |
| 35 | 500 |
| 40 | 400 |
| 45 | 354 |
| 50 | 297 |
| 60 | 250 |
| 70 | 210 |
| 80 | 177 |
| 100 | 149 |
| 120 | 125 |
| 140 | 105 |
| 170 | 88 |
| 200 | 74 |
| 230 | 63 |
| 270 | 53 |
| 325 | 44 |
| 400 | 37 |

Once the powdered sample such as nutritive media, media supplement, media subgroup or buffer (or mixture or combinations thereof) is placed into the fluid bed apparatus, it is subjected to suspension in an upwardly moving column of a gas, preferably atmospheric air or an inert gas such as nitrogen, and is passed through one or more particle filters. Alternatively, the gas or combination of gases used may be toxic or inhibitory to adventitious agents or toxins present in the sample. Since most dry powder, non-agglomerated nutritive media, media supplements, media subgroups and buffers are of a relatively small particle size, the filters used should be mesh screens that allow air to flow through but that retain the powders, for example filters of about 1-100 mesh, preferably about 2-50 mesh, more preferably about 2.5-35 mesh, still more preferably about 3-20 mesh or about 3.5-15 mesh, and most preferably about 4-6 mesh. Other filters may be used depending on the need and sample used, and can be determined by one skilled in the art.

Various embodiments disclosed herein relate, in part, to a nutritive medium powder comprising with one or more properties selected from the group consisting of an angle of repose between from about 10 to about 40 degrees; a bulk density between from about 0.001 g/cm3 to about 1 g/cm3; wherein 51% to 99% of particles are within a range of 30 to 100 mesh; wherein less than 10% of particles pass through a 200 mesh; and wherein the powder displays a flow measurement of about 3 to 5 kg.

Various embodiments disclosed herein provide dry powder nutritive media, media supplements, media subgroups, buffers and samples with particular sieve analysis characteristics or ranges of characteristics. For example, in various embodiments a dry powder nutritive media, media supplements, media subgroups, buffers or samples thereof will have sieve analysis characteristics wherein between from about 20% to about 80%, from about 40% to about 80%, from about 60% to about 80%, from about 20% to about 40%, from about 20% to about 60%, from about 40% to about 60%, from about 45% to about 55%, from about 47% to about 53%, from about 49% to about 51%, from about 50% to about 51%, or from 51% to 99% of the particles by mass are within the 30 to 200 mesh range, 40 to 200 mesh range, the 60 to 200 mesh range, the 100 to 200 mesh range, the 140 to 200 mesh range, 40 to 60 mesh range, 30 to 60 mesh range, 30 to 100 mesh range, 40 to 100 mesh range, 40 to 140 mesh range, 60 to 140 mesh range, 60 to 100 mesh range, 60 to 70 mesh range, 70 to 80 mesh range, 80 to 100 mesh range, 60 to 80 mesh range, 70 to 100 mesh range, 80 to 120 mesh range, 100 to 120 mesh range, 60 to 120 mesh range, 50 to 60 mesh range, 40 to 50 mesh range, 50 to 70 mesh range, 50 to 80 mesh range, 50 to 100 mesh range, 50 to 120 mesh range, 100 to 140 mesh range or 100 mesh. In some embodiments, a dry powder nutritive media, media supplements, media subgroups, buffers or samples will have sieve analysis characteristics wherein between from about 95% to about 99%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, or about 99% to about 100% of the particles are greater than or retained at the 200 mesh size (e.g., cumulative % retained).

In various embodiments, a dry powder nutritive media, media supplements, media subgroups, buffers or samples thereof will have sieve analysis characteristics wherein between from about 70% to about 100%, about 70% to about 97%, about 72% to about 97%, about 70% to about 94%, about 72% to about 94%, about 94% to about 97%, about 70% to about 80%, about 75% to about 85%, about 80% to about 90%, or about 85% to about 95%, or about 90% to about 100% of the particles are greater than or retained at the 100 mesh size.

In various embodiments, a dry powder nutritive media, media supplements, media subgroups, buffers or samples thereof will have sieve analysis characteristics wherein between from about 60% to about 100%, about 60% to about 97%, about 62% to about 96%, about 62% to about 89%, about 89% to about 96%, about 60% to about 70%, about 65% to about 75%, about 70% to about 80%, about 75% to about 85%, about 80% to about 90%, or about 85% to about 95%, or about 90% to about 100% of the particles are greater than or retained at the 80 mesh size.

In various embodiments, a dry powder nutritive media, media supplements, media subgroups, buffers or samples thereof will have sieve analysis characteristics wherein between from about 40% to about 95%, about 40% to about 90%, about 44% to about 90%, about 40% to about 89%, about 44% to about 89%, about 70% to about 95%, about 70% to about 90%, about 72% to about 90%, about 72% to about 89%, about 40% to about 75%, about 40% to about 72%, about 44% to about 72%, about 44% to about 75%, about 40% to about 45%, about 45% to about 50%, about 50% to about 55%, about 55% to about 60%, about 60% to about 65%, about 65% to about 70%, about 70% to about 75%, or about 75% to about 80%, about 80% to about 85%, about 85% to about 90% or about 90% to about 95% of the particles are greater than or retained at the 60 mesh size.

In various embodiments, a dry powder nutritive media, media supplements, media subgroups, buffers or samples thereof will have sieve analysis characteristics wherein between from about 10% to about 38%, about 12% to about 38%, about 10% to about 35%, about 12% to about 35%, about 10% to about 15%, about 15% to about 20%, about 20% to about 25%, about 25% to about 30%, about 30% to about 35%, or about 35% to about 40% of the particles are greater than or retained at the 45 mesh size.

In various embodiments, a dry powder nutritive media, media supplements, media subgroups, buffers or samples thereof will have sieve analysis characteristics wherein between from about 7% to about 31% retained at the 30 mesh size and above; about 18% to about 73% retained at the 45 mesh size and above; about 33% to about 92% retained at the 60 mesh size and above; about 56% to about 97% retained at the 80 mesh size and above; about 68% to about 98% retained at the 100 mesh size and above; about 96% to about 100% retained at the 200 mesh size and above; about 0.15% to about 3.7% retained below the 200 mesh size.

In various embodiments, between from about 40% to about 60% of the particles by mass will be between the 60-100 mesh range. In various embodiments, between from about 40% to about 60% of the particles by mass will be between the 40-100 mesh range.

In various embodiments, between from about 40% to about 60% of the particles by mass will be between the 60-140 mesh range. In various embodiments, between from about 40% to about 60% of the particles by mass will be between the 50-120 mesh range. In various embodiments, between from about 40% to about 60% of the particles by mass will be between the 50-100 mesh range. In various embodiments, between from about 40% to about 60% of the particles by mass will be between the 60-120 mesh range.

In various embodiments, the dry powder nutritive media, media supplements, media subgroups, buffers or samples thereof will have sieve analysis characteristics wherein equal to or less than 0.001%, 0.01%, 0.1%, 0.2%, 0.3%, 0.4%, 0.5%, 0.6%, 0.7%, 0.8%, 0.9%, 1%, 2%, 3%, 4%, 4.1%, 5%, 6%, 7%, 8%, 9%, or 10%, or between from about 0.001% to about 0.005%, from about 0.001% to about 0.0025%, from about 0.0025% to about 0.005%, from about 0.005% to about 0.01%, from about 0.005% to about 0.0075%, from about 0.0075% to about 0.01%, from about 0.01% to about 0.05%, from about 0.01% to about 0.025%, from about 0.025% to about 0.05%, from about 0.05% to about 0.1%, from about 0.05% to about 0.075%, from about 0.075% to about 0.1%, from about 0.1% to about 0.5%, from about 0.1% to about 0.25%, from about 0.25% to about 0.5%, from about 0.5% to about 1%, from about 0.5% to about 0.75%, from about 0.75% to about 1%, from about 1% to about 10%, from about 2% to about 10%, from about 3% to about 10%, from about 4% to about 10%, from about 5% to about 10%, from about 6% to about 10%, from about 7% to about 10%, from about 8% to about 10%, from about 9% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 2% to about 8%, from about 3% to about 7%, from about 4% to about 6%, from about 3% to about 5%, from about 4% to about 5%, from about 3% to about 4%, from about 2% to about 3%, from about 6% to about 7%, from about 7% to about 8%, from about 8% to about 9%, from about 3% to about 5%, from about 5% to about 7%, from about 6% to about 8%, or from about 7% to about 9% of the particles, by mass, pass through the 140, 170, 200, 230, 270, 325, 400, 450, 500 or 635 mesh.

In-Line Dry Media Rehydration System

In one aspect, a "plug and go" in-line powder to liquid media mixing system that is cost effective and eliminates operational steps that can introduce sources of operator error and contamination when liquid media is prepared from bulk dry media sources (e.g., powders, granules, AGT, etc.), is disclosed.

As used herein, a "plug and go" media mixing system is one where the operator can simply insert a package containing media into a system that automates certain operational steps resulting in a final rehydrated media product. As discussed above, "plug and go" mixing systems offer advantages in ease of media production scalability and preventing contamination without the need for operating the mixing systems in steam-in-place (SIP) or clean-in-place (CIP) type environments. In various embodiments, the mixing system can be easily scaled up to produce liquid media from a volume of 1 L to a volume of at least 5000 L or more, and when more than one "plug and go" mixing system is required the system can be scaled up in either a series configuration or a parallel system configuration.

The in-line "plug and go" liquid media mixing systems described herein moves the mixing of the AGT, DPM, or other powdered nutritive media and solvent out of the container (e.g., capsule, tank, bag, etc.) and puts it in an in-line flow stream of solvent (e.g. water, etc.) effectively eliminating several steps in the user's media preparation operation. Also, the system can be driven with a standard peristaltic pump already in the possession of most users. Alternatively, pumps can be purchased at a fraction of the investment required for the above methods. In various embodiments, the powdered medium can be metered at a defined pace to ensure complete solubilization of the powdered medium into the solvent. In various embodiments, the mixing system incorporates an in-line static mixing device to ensure hydration. In various embodiments, the system can combine a dry media component configured to meter the delivery of dry powder media with an in-line static mixing device. In various embodiments, the volume of liquid media handled by the mixing system can be scaled from at least 1 L to 5000 L or more. The embodiments provided herein can optionally incorporate a sterile filter in-line thereby providing a media hydration and sterilization system in a single pass thus eliminating the need for the use of mixing impellers. The various embodiments disclosed herein can provide an in-line dry powder media mixing and/or filtering system from granule (media) to bioreactor within a few feet of tubing.

The in-line systems and methods described herein can be specially constructed for mixing agglomerated media (AGT) or any dry powder medium (DPM). Various embodiments may exploit the ease of solubility properties of AGT. Once the AGT comes in contact with water it begins to solubilize. In various embodiments, the system comprises a disposable static mixing element which can be placed directly downstream of the metering device and is in-line. In addition, the user can place a sterile filtering device in-line downstream of the static mixer thereby providing sterile, ready to use media in one single pass of the full water volume. The static mixing element ensures full hydration of the AGT. In various embodiments, this media can be stored in a bag or sent directly to a sterile bioreactor. Any of the operations that form part of the embodiments described herein are useful operations. The various embodiments described herein, can be practiced as a stand-alone product or can be combined with other mixing systems.

Media Mixing Vessel

FIG. 1 is a schematic diagram of a media mixing vessel 100 for preparing liquid media from dry bulk storage forms (e.g., powders, granules, etc.) of media ('Dry Media'), in accordance with various embodiments. Media mixing vessels 100 are especially useful in the biotech industry because they can be used to provide prepackaged dry media in a format that can be quickly rehydrated free of issues with operator error found in more conventional media rehydration systems using mixing tanks and reactors. Examples of operator error can include inaccurate weighing of the dry media powder, spillage, operator introduced contamination, etc. Once the contents of media vessel 100 have been rehydrated, the vessel 100 can be disposed of and replaced with a fresh media mixing vessel 100.

According to various embodiments, a media mixing vessel 100 can be comprised of a flexible portion 102 (e.g., flexible bag, liner, etc.), a fluid inlet 104 and a fluid outlet 108. In various embodiments, the fluid inlet 104 can include a nozzle 106. The nozzle 106 can face an interior volume of the flexible portion 102. The fluid outlet 108 can include a filter element 110 that is configured to prevent dry media exceeding a predetermined size from exiting the flexible portion 102. In various embodiments, the filter element 110 is configured to screen out dry media particles larger than about 50 microns, larger than about 40 microns, larger than about 30 microns, larger than about 20 microns or larger than about 10 microns. In various embodiments, the size range of dry media particles screened out by filter element 110 can be between about 10 microns to about 200 microns. In various embodiments, the size range of dry media particles screened out by filter element 110 can be between about 50 microns to about 100 microns. In various embodiments, the filter element 110 can be comprised of polyethylene, metal-based mesh, etc. However, it should be appreciated that the filter element 110 can be comprised of any known material as long as the resulting filter element 110 can be utilized for its intended purpose of filtering out media granules or agglomeration exceeding a certain predetermined size.

In various embodiments, a gas vent 112, such as a bleed valve or microporous hydrophobic membrane, can be operably coupled to the flexible portion and configured to evacuate gas (e.g., trapped air, etc.) from the flexible portion 102 when the flexible portion 102 is filled with liquid (i.e., mixing fluid). Examples of liquids that can be use dot rehydrate media includes, but are not limited to: water, buffer solutions, etc. In various embodiments the vent 112 can be comprised of polyethylene, rubber, metal etc. and can be held in place by any conventional useful means such as by a sleeve that extends around the sidewall portion or secured by any other means capable of securing the vent 112 to the flexible portion 102. In various embodiments, the vent 112 can be configured to be a one-way valve that is designed to release gas from the flexible portion 102 while it is being filled with mixing fluid and at the same time functioning as a contamination prevention barrier (e.g., prevent ingress of outside air, moisture, bacteria and other contaminants). In various embodiments, a fill port 114 can be operably coupled to the flexible portion 102 and configured to be sealed after the flexible portion 102 has been filled with dry powdered media. The fill port 114 can be comprised of plastic, rubber, metal, or any other material that is known or useful in the art. Additionally, the fill port 114 can comprise an opening in the flexible portion 102 and a means to seal the opening. This means the fill port 114 can be sealed using various means, including, but not limited to: glue, sealants, heat-sealing, solid plugs, etc. In various embodiments, the post filling seal is a hermetic seal.

In various embodiments, the vent 112 can be positioned on a side opposite that of the fluid outlet 108. In this configuration mixing liquid can enter the flexible portion 102 via the fluid inlet 104 at the same time that air is evacuated through the vent 112. In various embodiments, the vent 112 can be positioned so that it is positioned at the high point of the flexible portion 102 relative to the fluid inlet 104 and/or the fluid outlet 108 in order to maximize air evacuation during filling. In various embodiments, vent 112 can be configured to allow for only air to evacuate while retaining all the liquid within the flexible portion 102.

The flexible portion 102 can be comprised of polymer materials (e.g., LDPE, etc.), rubber, composite, USP Class VI materials, etc., or any combination thereof. In various embodiments, the flexible portion 102 is comprised of sheets having a thickness in a range of between about 0.1 mm to about 0.5 mm, or between about 0.2 mm to about 2 mm. Other thicknesses can also be used. The material can be comprised of a single ply material or can comprise two or more layers which are either sealed together or separated to form a double wall container. Where the layers are sealed together, the material can comprise a laminated or extruded material. The laminated material can include two or more separately formed layers that are subsequently secured together by an adhesive. The extruded material can include a single integral sheet having two or more layers of different material that are each separated by a contact layer. All of the layers can be simultaneously co-extruded. One example of an extruded material that can be used is the HyQ CX3-9 film available from HyClone Laboratories Inc., out of Logan, Utah. The HyQ CX3-9 film is a three layer 9 mil cast film. The outer layer is a polyester elastomer coextruded with an ultra-low density polyethylene product contact layer. Another example of an extruded material that can be used is the HyQ CX5-14 cast film also available from HyClone Laboratories, Inc. The HyQ CX5-14 cast film comprises a polyester elastomer outer layer, an ultra-low density polyethylene contact layer, and an EVOH barrier layer disposed therebetween. In another example, a multi-web film produced from three independent webs of blown film can be used. The two inner webs are each a 4 mil monolayer polyethylene film (which is referred to by HyClone as the HyQ BM1 film) while the outer barrier web is a 5.5 mil thick 6-layer coextrusion film (which is referred to by HyClone as the HyQ BX6 film).

Ideally, the flexible portion 102 is comprised of materials that are not chemically reactive with the dry media, media mixing fluids or the resultant liquid media from the media rehydration operation. That is, the flexible portion 102 materials do not leach or release residues into the rehydrated media after the media rehydration process is complete. In various embodiments, the flexible portion 102 can be filled with pre-sterilized dry media. In various embodiments, the flexible portion 102 can be filled with non-sterilized dry media, which can later be sterilized with radiation or other means. In various embodiments, the flexible portion 102 is comprised of materials that will not degrade or be compromised from sterilizing irradiation or heat. It various embodiments, the flexible portion 102 can also include additional ports and tubing for headspace gas, thermo well, titrant, sampling and various pulse feeds.

In various embodiments the flexible portion 102 can be pre-filled with dry media, thus eliminating the need for an operator to weigh and fill the flexible portion 102 with media prior to use. The dry media can be AGT, DPM, or any other bulk storage forms of dry nutritive media.

In various embodiments the media can be comprised of particles of about 150 to about 15,000 microns in size. In various embodiments the media can be comprised of particles of about 300 to about 15,000 microns in size. In various embodiments the media can be comprised of particles of about 150 to about 300 microns in size. The granular size of the individual media particles can be determined by the dry media type (e.g., AGT, DPM, etc.), particular application, or can be designed to work in conjunction with filter element 110. It should be appreciated that the granular size will generally depend on the ingredients that the dry media is comprised of. In various embodiments, the filter element 110 can be configured to allow particles of a predetermined size to pass through while preventing media particles that exceed the predetermined (i.e., considered too large) to pass. Media particles can be considered too large for a variety of reasons including causing incomplete rehydration/mixing, causing clogs in downstream system components (e.g., sterile filters, valving, etc.), etc.

In various embodiments, a nozzle 106 can be configured to supply mixing fluid to dissolve dry media in a single pass. This can be advantageous because it can reduce the time required to solubilize dry media as well as eliminating extra system components and/or processing steps that would otherwise need to be included (such as additional mixing elements or steps). Specifically, the use of a nozzle 106 configured with the various operational characteristics outlined below can remove the need for an impeller or other internal mixing device once the flexible portion 102 has been filled with mixing liquid. In various embodiments, the nozzle 106 is configured to supply mixing fluid to the flexible portion 102 while minimizing the level of foam generated as dry media is solubilized by the mixing fluid.

In various embodiments the nozzle 106 can be comprised of an eductor or equivalent device configured to entrain (i.e., recirculate) liquid in the flexible portion 102 as motive (supply) liquid moves through the nozzle 106. In various embodiments, nozzle 106 can be configured to produce an entrainment ratio (i.e., volume of recirculating fluid to motive or supply fluid) of at least about 5 parts recirculating fluid to about 1 part motive fluid. This ratio can change depending on the type of dry media that is being rehydrated and/or the specific application. For example, the circulation (or fluid entrainment) ratio can be 1:1, 2:1, 3:1, 4:1, 5:1, or any other ratio that is available and useful depending on the particular application. The entrainment ratio that a nozzle 106 is configured to produce is important because it relates to the amount of media mixing and agitation that occurs within the flexible portion 102. That is, entrainment causes additional mixing of partially solubilized media as the dry media is solubilized by liquid entering the flexible portion 102. In various embodiments, nozzle 106 has an orifice diameter that can directly impact the velocity of mixing fluid that flows through nozzle 106 into the flexible portion 102 at any given fluid supply flow rate. That is, mixing fluid velocity through the nozzle 106 is equal to the flow rate divided by the orifice area (as determined from the orifice diameter). It is a direct estimate of the velocity of mixing fluid being supplied to the flexible portion 102 by the nozzle 106, as expressed in Equation 1:

$$\text{Eductor Mixing Fluid Velocity (Orifice Velocity)} = \frac{\text{Mixing Fluid Flow Rate}}{\text{Eductor Orifice Area}} \quad \text{Equation 1}$$

The nozzle's 106 orifice diameter can depend on a variety of factors including, but not limited to, the specific application that the media vessel is being used for, the size of the flexible portion 102, fluid supply pressure, fluid supply flow rate, etc. However, the critical defining operational requirement for nozzle 106 is that it supplies mixing fluid to the flexible portion 102 with sufficient flow power to substantially solubilize (effectively mix) the dry media contained in the flexible portion 102. As used herein, flow power can be defined as one-half the mixing fluid flow rate times the mixing fluid velocity squared. It is an estimate of the power imparted by the fluid mass being supplied by the nozzle 106 to the flexible portion 102, as expressed in Equation 2:

$$\text{Flow Power} = \left(\frac{\text{Mixing Fluid Flow Rate}}{2}\right) \times (\text{Eductor Mixing Fluid Velocity})^2 \quad \text{Equation 2}$$

In various embodiments, the nozzle 106 orifice has a diameter of between about 1.0 millimeters (mm) to about 10 mm. In various embodiments, the nozzle 106 orifice has a diameter of between about 3.0 mm to about 6.0 mm. In various embodiments, the nozzle 106 orifice has a diameter of between about 6.0 mm to about 10.0 mm.

In various embodiments, a nozzle 106 with an orifice diameter of between about 1.0 mm to about 10 mm is configured to supply fluid to the flexible portion 102 with a flow power of at least about 10 Watts (W). In various embodiments, a nozzle 106 with an orifice diameter of between 3 mm to about 6 mm is configured to supply fluid to the flexible portion 102 with a flow power of at least about 15 W. In various embodiments, a nozzle 106 with an orifice diameter of between about 6 mm to about 10 mm is configured to supply fluid to the flexible portion 102 with a flow power of at least about 10 W. In various embodiments, the nozzle 106 can be configured to supply fluid to the flexible portion 102 with a flow power of between about 5 W to about 25 W. In various embodiments, the nozzle 106 can be configured to supply fluid to the flexible portion 102 with a flow power of between about 10 W to about 15 W.

In various embodiments, a nozzle 106 with an orifice diameter of between about 1.0 mm to about 10 mm is configured to supply fluid to the flexible portion 102 with an average mixing velocity of between about 7 meters per second (m/s) to about 19 m/s. In various embodiments, a nozzle 106 with an orifice diameter of between 3 mm to about 6 mm is configured to supply fluid to the flexible portion 102 with an average mixing velocity of between about 14 m/s to about 19 m/s. In various embodiments, a nozzle 106 with an orifice diameter of between about 6 mm to about 10 mm is configured to supply fluid to the flexible portion 102 with an average mixing velocity of between about 7 m/s to about 14 m/s.

In various embodiments, a nozzle 106 with an orifice diameter of between about 1.0 mm to about 10 mm is supplied with mixing fluid at a rate of between about 1 liter per minute (LPM) to about 75 LPM. In various embodiments, a nozzle 106 with an orifice diameter of between 3 mm to about 6 mm is supplied with mixing fluid at a rate of between about 5 LPM to about 35 LPM. In various embodiments, a nozzle 106 with an orifice diameter of between about 6 mm to about 10 mm is supplied with mixing fluid at a rate of between about 5 LPM to about 35 LPM.

In various embodiments, a nozzle 106 with an orifice diameter of between about 1.0 mm to about 10 mm is supplied with mixing fluid at a fluid pressure of between about 1 pound per square inch (psi) to about 60 psi. In various embodiments, a nozzle 106 with an orifice diameter of between 3 mm to about 6 mm is supplied with mixing fluid at a fluid pressure of between about 10 psi to about 40 psi. In various embodiments, a nozzle 106 with an orifice diameter of between about 6 mm to about 10 mm is supplied with mixing fluid at a fluid pressure of between about 5 psi to about 15 psi.

In various embodiments the fluid outlet 108 can serve as conduit to dispense solubilized media. In various embodiments, there can be an additional valve preventing premature dispensing of partially solubilized media that can open upon complete dry media mixing.

Single-Vessel Media Mixing Container System

As previously discussed, the media mixing vessel 100 can be a component of an integrated media mixing system.

Figure 2:
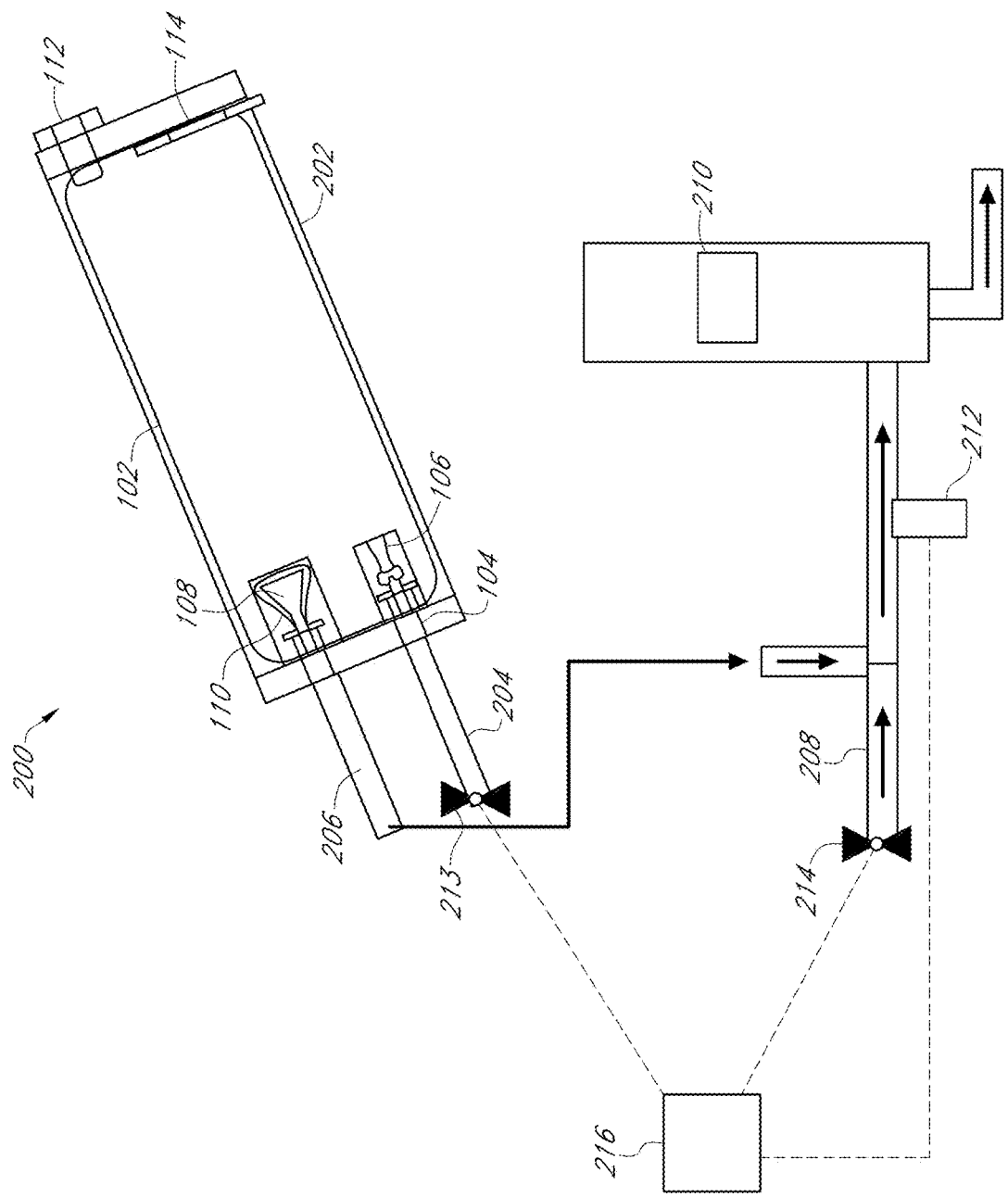
FIG. 2 is a schematic diagram of a media mixing container system, in accordance with various embodiments.
Figure 3A:
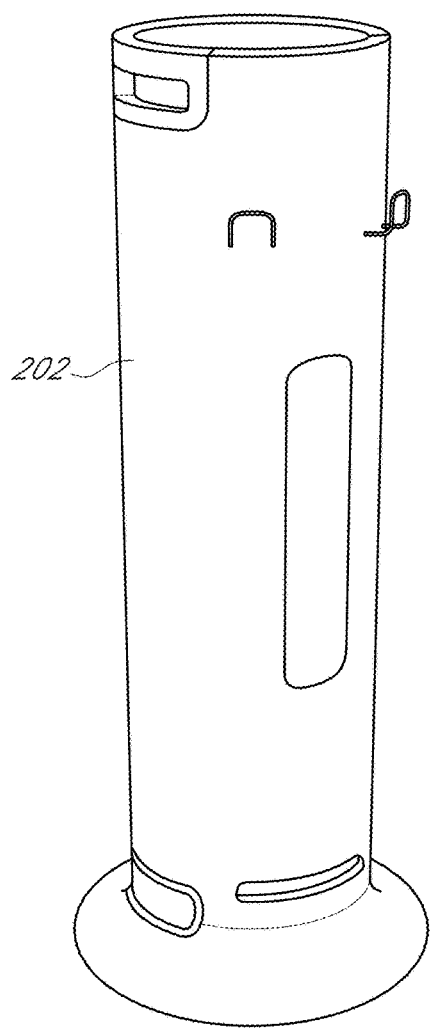
FIGS. 3 A-D are illustrations of a first media mixing container system, in accordance with various embodiments.
Figure 3B:
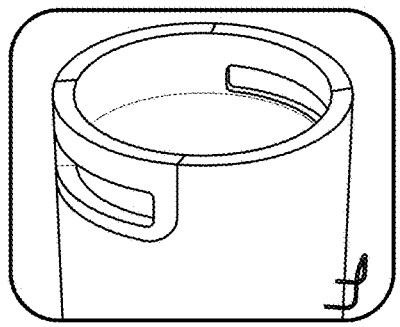
Figure 3C:
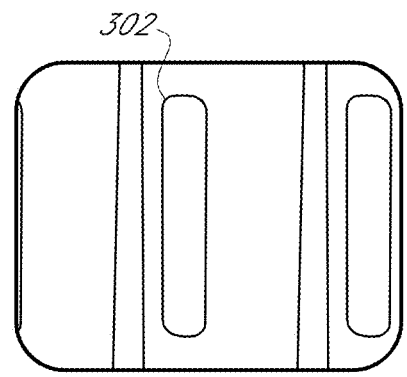
Figure 3D:
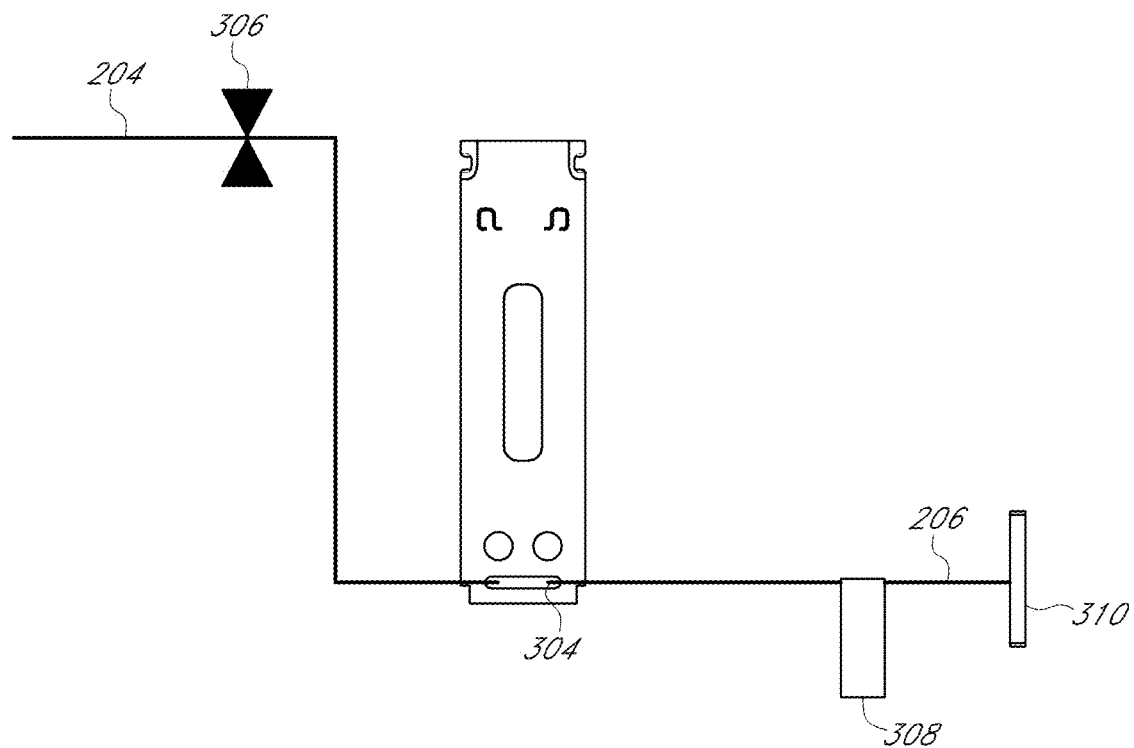
Figure 4A:
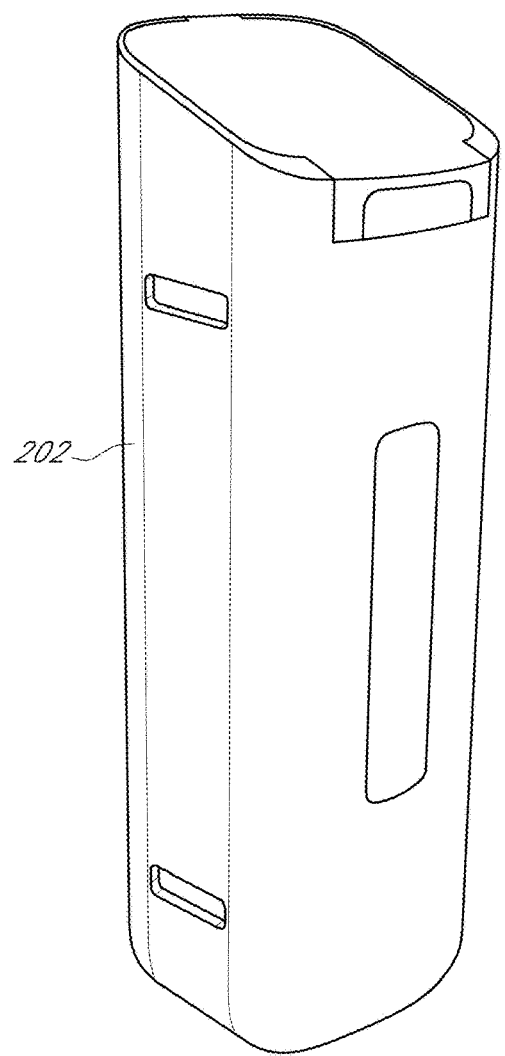
FIGS. 4 A-D are illustrations of a second media mixing container system, in accordance with various embodiments.
Figure 4B:
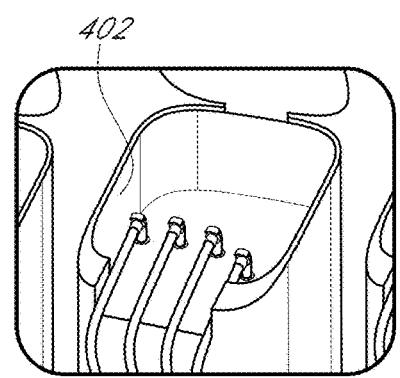
Figure 4C:
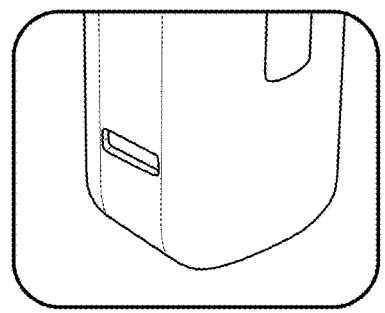
Figure 4D:
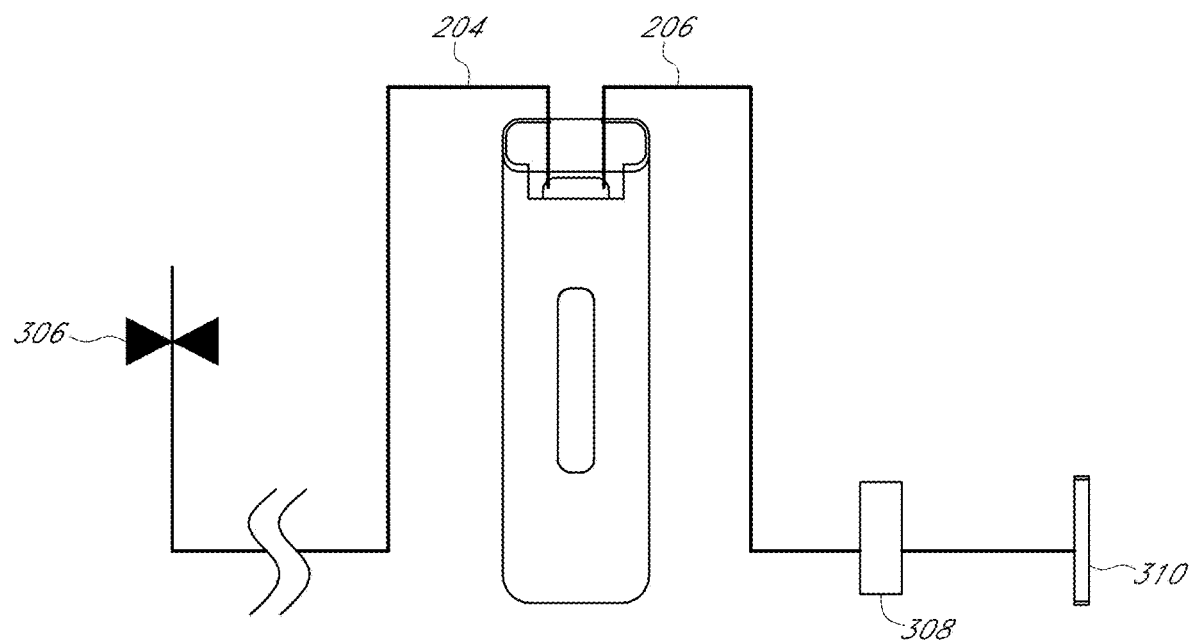
Figure 5A:
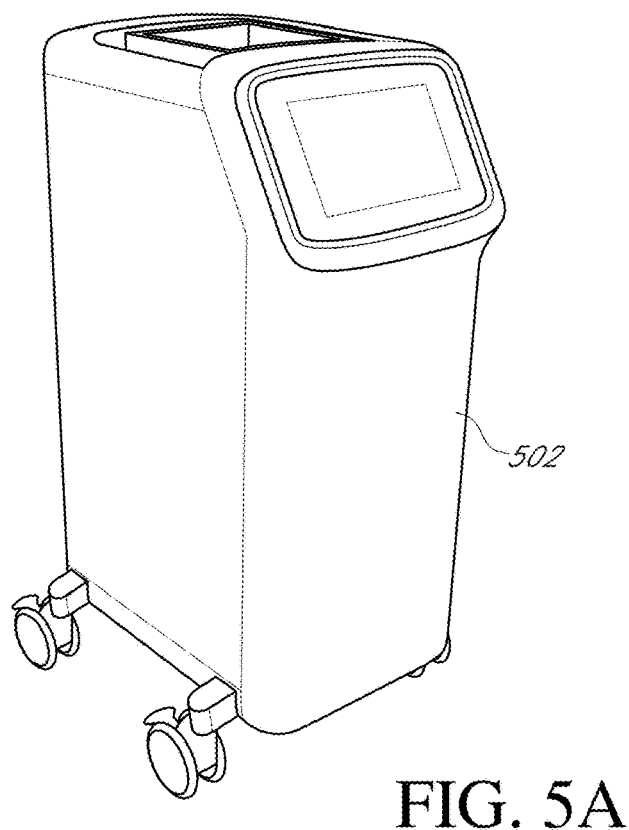
FIGS. 5 A-F are illustrations of a third media mixing container system, in accordance with various embodiments.
Figure 5B:
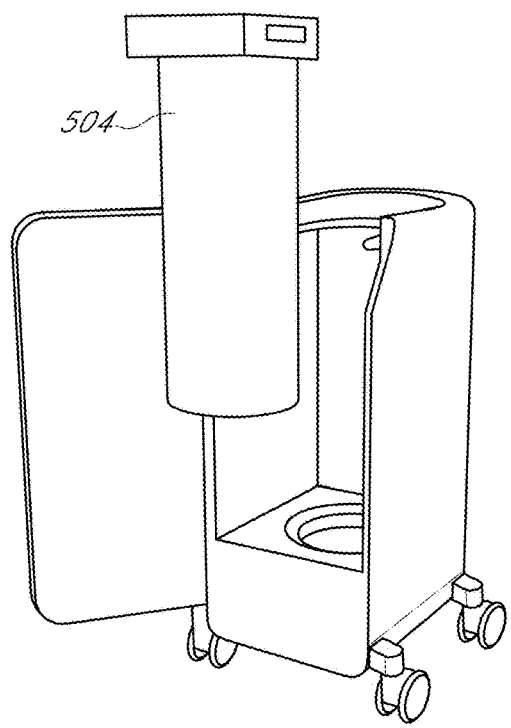
Figure 5C:
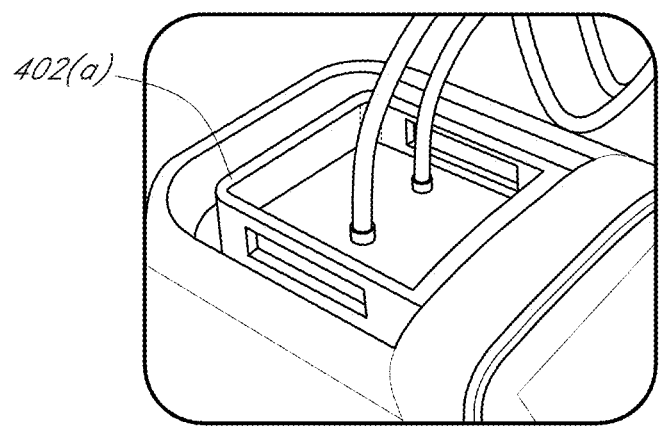
Figure 5D:
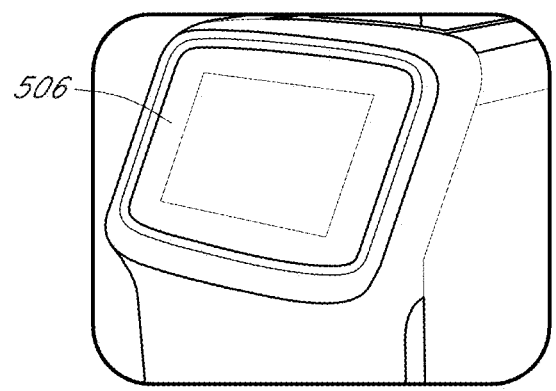
Figure 5E:
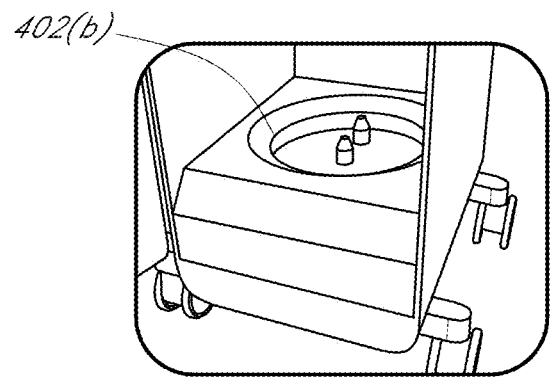
Figure 5F:
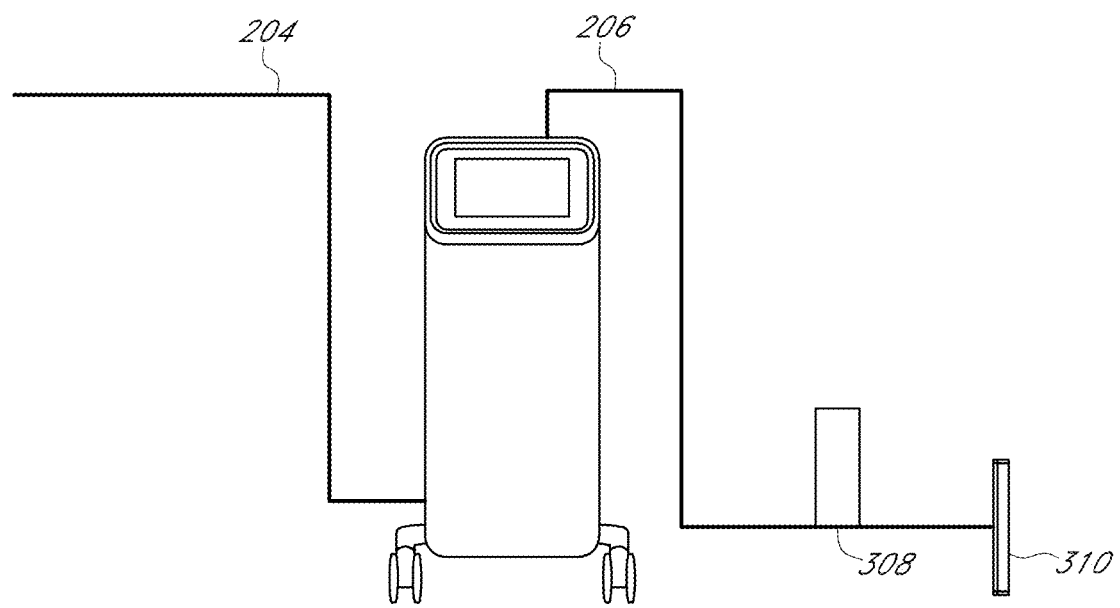

FIG. 2 is a schematic diagram of a media mixing container system, in accordance with various embodiments. As shown herein, in one aspect, media mixing system 200 can comprise a rigid container 202 that includes a flexible portion 102 (i.e., flexible media mixing vessel). The rigid container 202 can be comprised of a variety of different types of materials including, but not limited to: rigid plastic, metal, glass, composites, carbon fiber, USP Class VI materials, etc. It should be understood, however, that the rigid container 202 can be comprised of essentially any material as long as the resulting container 202 can provide the requisite support for the flexible portion 102 during media rehydration.

In various embodiments, rigid container 202 has a first volumetric capacity and flexible portion 102 has a second volumetric capacity that is larger than the first volumetric capacity. In various embodiments, rigid container 202 has a first volumetric capacity and flexible portion 102 has a second volumetric capacity that is about the same as the first volumetric capacity. In various embodiments, the inner wall of the rigid container 202 can be configured to provide lateral or structural support for the flexible media vessel 100.

In various embodiments, the flexible portion 102 can be pre-filled with dry media, thus eliminating the need for an operator to weigh and fill the flexible portion 102 with media prior to use. The media mixing system 200 can then provide the mixing fluid necessary to rehydrate and dispense the solubilized media at a specified concentration. The dry media can be AGT, DPM, or any other bulk storage forms of dry nutritive media.

In various embodiments, flexible media vessel 100 can be inserted or fit into the rigid container 202 and then removed after use (i.e., a media rehydration operation). For example, once the media has been dispensed through the fluid outlet 108 the flexible media vessel 100 can be thrown away and later replaced with a fresh flexible portion 102.

In various embodiments, the flexible portion 102 can be filled with pre-sterilized dry media. In various embodiments, the flexible portion 102 can be filled with non-sterilized dry media, which can later be sterilized with radiation or other means. That is, the dry media can be sterilized using one or more types of media sterilization techniques (e.g., irradiation, heat, etc.) while it is stored in the flexible portion 102. In various embodiments, the flexible portion 102 is comprised of materials that will not degrade or be compromised from sterilizing irradiation or heat.

In various embodiments the media can be comprised of particles of about 150 to about 15,000 microns in size. In various embodiments the media can be comprised of particles of about 300 to about 15,000 microns in size. In various embodiments the media can be comprised of particles of about 150 to about 300 microns in size. It should be understood that the granular size of the individual media particles can be determined by the dry media type (e.g., AGT, DPM, etc.), particular application, or can be designed to work in conjunction with filter element 110.

In various embodiments, media mixing system 200 can further comprise a fluid supply line 204 that can be fluidically connected to the flexible media vessel 102 and configured to supply a mixing fluid to the flexible media vessel 102. In various embodiments, a fluid dispensing line 206 can be fluidically connected to the flexible media vessel 102 and configured to dispense solubilized media from the flexible media vessel 102. In various embodiments, a fluid dilution line 208 can be connected to the fluid dispensing line 206 and configured to supply additional mixing fluid to further dilute the solubilized media in the fluid dispensing line 206 to a predetermined concentration.

In various embodiments, a filter element 210 can be fluidically connected to the fluid dispensing line 206 and be configured to sterilize solubilized media dispensed from the flexible portion 102. In various embodiments, the filter element 210 can be configured to secondarily filter out or prevent particles larger than a predetermined size. In various embodiments, system 200 can include a fluid supply flow control valve 213 that is fluidically connected to the fluid supply line 204 and a fluid dilution flow control valve 214 that is fluidically connected to the fluid dilution line 208. In various embodiments, the fluid supply flow control valve 213 and/or the fluid dilution control valve 214 are manually controlled by an operator. In various embodiments, the fluid supply flow control valve 213 and/or the fluid dilution control valve 214 are configured to function as time-delayed automated flow control valves (e.g., automated solenoid valve, etc.) that can adjust the flow rate of mixing fluid supplied to the fluid supply line 204 and/or the fluid dilution line 208 according to one or more pre-defined time intervals. That is, the fluid supply flow control valve 213 and the fluid dilution flow control valve 214 can be individually programmed by an operator to increase or decrease the flow rates of mixing fluid supplied to the fluid supply line 204 and/or the fluid dilution line 208 based on a number of different time points during the dry media rehydration process. In various embodiments, the functionalities of the fluid supply flow control valve 213 and the fluid dilution flow control valve 214 can be provided by a single integrated fluid flow control valve module.

In various embodiments, the system 200 can additionally include a sensor element 212 that can be placed adjacent to or upstream from the filter element 212. In various embodiments, the sensor element 212 is in direct communication with the fluid supply flow control valve 213 and the fluid dilution flow control valve 214 and is configured to provide various types of sensor measurements to the valves in order to trigger their activation or deactivation.

In various embodiments, the sensor element 212 is a pressure transducer configured to measure fluid pressure of the fluid dispensing line 206 and generate communication signals (either electrically or mechanically) that can activate the fluid supply 213 and/or the fluid dilution 214 flow control valves to open or close, thereby, increasing or decreasing the flow rate of mixing fluid supplied to the fluid supply line 204 and/or the fluid dilution line 208. In various embodiments, the sensor element 212 is a conductivity sensor configured to measure the fluid conductivity of the solubilized media in the fluid dispensing line 206 and communicate those measurements back to the fluid supply 213 and/or fluid dilution 214 flow control valves to increase or decrease the flow rate of mixing fluid supplied to the fluid supply line 204 and/or the fluid dilution line 208. In various embodiments, the sensor element 212 is an optical sensor configured to measure a concentration of the solubilized media in the fluid dispensing line 206 and communicate those measurements back to the fluid supply 213 and/or fluid dilution 214 valves to increase or decrease the flow rate of mixing fluid supplied to the fluid supply line 204 and/or the fluid dilution line 208.

In various embodiments, the system 200 additionally includes a system control component 216 that is communicatively connected to the fluid supply flow control valve 213 and/or the fluid dilution flow control valve 214. In various embodiments, the system control component 216 can be configured to provide instructions to increase or decrease the flow rates of mixing fluid supplied to the fluid supply line 204 and/or the fluid dilution line 208 based on one or more pre-defined time intervals or time point settings.

In various embodiments, system 200 can also include a system control component 216 that can be configured to receive information from the sensor element 212 and then send a signal to activate the fluid supply 213 and/or fluid dilution 214 flow control valves to increase or decrease the flow rate of mixing fluid supplied to the fluid supply line 204 and/or the fluid dilution line 208. In various embodiments, automated valves 213 and 214 can be completely closed and sometimes they can be completely open. Having an adjustable flow rate can serve a variety of purposes as explained below.

It should be appreciated that various other types of sensor elements 212 can be used in system 200 provided that the sensor can measure a physicochemical property of the solubilized media in fluid dispensing line 206 that is relevant to the rehydration of the dry media.

The purpose for increasing or decreasing the flow rate of mixing fluid supplied to the fluid supply 204 or dilution line 208 can be to ensure that the solubilized media reaches a preferred concentration. Generally, the preference can be based on what the media is ultimately used for and can result in a 1× solution, however, various embodiments can produce higher concentrations.

Another reason for increasing or decreasing mixing fluid supplied to the fluid supply 204 or dilution line 208 can be the unclogging of complete or partial blockages that have occurred in the media mixing system 200. It is possible that blockages can occur at the filter element 210 and that decreasing the concentration of solubilized media can unclog the complete or partial blockage.

In various embodiments the fluid supply line 204 can be directly connected to the fluid inlet 104. For example, the fluid supply line 204 and the fluid inlet 104 can have hoses that can attach directly to one another.

In various embodiments, the fluid supply line 204 can be connected to fluid inlet 104 through a coupling device using an adapter fitting. The adapter fitting can be an additional component or the fitting could be built into the rigid container 202.

In various embodiments, the fluid inlet 104 can be connected to a first adapter and the fluid supply line 204 can be connected to a second adapter that is in fluid communication with the first adapter. For example, the two adapters can be quick connect adapters that can physically be attached to one another or there can be an intermediate component that allows fluid communication to occur. It will be obvious to a skilled artisan that a multitude of plumbing options exist to create fluidic connectivity throughout the system.

In various embodiments, the fluid dispensing line 206 can be directly connected to the fluid outlet 108. In various embodiments, the fluid dispensing line 206 and the fluid outlet 108 can have hoses that can attach directly to one another. In various embodiments, the fluid dispensing line 206 and the fluid outlet 108 can be one piece.

In various embodiments, the fluid dispensing line 206 can be connected to the fluid outlet 108 through a coupling device such as a fitting. For example, the fitting can be an additional component or the fitting could be built into the rigid container 202.

In various embodiments, the fluid outlet 108 can be connected to a first adapter and the fluid dispensing line 206 can be connected to a second adapter that is in fluid communication with the first adapter. For example, the two adapters can physically attach to one another or there can be an intermediate component that allows fluid communication to occur. It will be obvious to a skilled artisan that a multitude of plumbing options exist to create fluidic connectivity throughout the system.

As mentioned above, in various embodiments, the media mixing vessel 102 can be oriented such that the vent 112 is elevated relative to the fluid outlet 108.

In various embodiments, the media mixing system 200 can be used to rehydrate dry media that is agglomerated. However, various other known and useful media types can also be used in various embodiments.

In various embodiments, the media mixing system 200 can incorporate a nozzle 106 that can be configured to supply mixing fluid to dissolve dry media in a single pass. This can be advantageous because it reduces time required to solubilize media as well as extra parts that would otherwise need to be included. Furthermore, it removes the need for any additional impeller or internal mixing device which in some of the prior art is required once a mixing container has been filled. As mentioned above, AGT can be used in such embodiments.

In another aspect, media mixing system 200 can comprise a rigid container 202 that can be directly filled with dry media. That is, the rigid container 202 can be filled with dry media without utilizing a flexible media portion 102 (i.e., flexible media mixing vessel). Ideally, the rigid container 202 is comprised of materials that are not chemically reactive with the dry media, the media mixing fluids or the resultant liquid media from the media rehydration operation. That is, the rigid container 202 materials do not leach or release residues into the rehydrated media after the media rehydration process is complete. In various embodiments, the rigid container 202 can be pre-filled with dry media, thus eliminating the need for an operator to weigh and fill container 202 with media prior to use.

In various embodiments, the rigid container 202 can be filled with pre-sterilized dry media. In various embodiments, the rigid container 202 can be filled with non-sterilized dry media, which can later be sterilized with radiation or other means. That is, the dry media can be sterilized using one or more types of media sterilization techniques (e.g., irradiation, heat, etc.) while it is stored in the rigid container 202. In various embodiments, the rigid container 202 is comprised of materials that will not degrade or be compromised from sterilizing irradiation or heat.

In various embodiments, the rigid container 202 can further include a fluid inlet and a fluid outlet. The fluid inlet can include a nozzle which faces an interior volume of the rigid container 202. The fluid outlet can include a filter element that is configured to prevent dry media exceeding a predetermined size from exiting the rigid container 202. In various embodiments, the filter element is configured to screen out dry media particles larger than about 50 microns, larger than about 40 microns, larger than about 30 microns, larger than about 20 microns or larger than about 10 microns. In various embodiments, the size range of dry media particles screened out by filter element can be between about 10 microns to about 200 microns. In various embodiments, the size range of dry media particles screened out by filter element can be between about 50 microns to about 100 microns. In various embodiments, the filter element can be comprised of polyethylene, metal-based mesh, etc. However, it should be appreciated that the filter element can be comprised of any known material as long as the resulting filter element can be utilized for its intended purpose of filtering out media granules or agglomeration exceeding a certain predetermined size.

In various embodiments, a gas vent, such as a bleed valve or microporous hydrophobic membrane, can be operably coupled to the rigid container 202 and configured to evacuate gas (e.g., trapped air, etc.) from the rigid container when the rigid container is filled with liquid (i.e., mixing fluid). Examples of liquids that can be use dot rehydrate media includes, but are not limited to: water, buffer solutions, etc. In various embodiments the vent can be comprised of polyethylene, rubber, metal etc. and can be held in place by any conventional useful means such as by a sleeve that extends around the sidewall portion or secured by any other means capable of securing the vent to the rigid container 202. In various embodiments, the vent can be configured to be a one-way valve that is designed to release gas from the rigid container while it is being filled with mixing fluid and at the same time functioning as a contamination prevention barrier (e.g., prevent ingress of outside air, moisture, bacteria and other contaminants). In various embodiments, a fill port can be operably coupled to the rigid container and configured to be sealed after the rigid container has been filled with dry powdered media. The fill port can be comprised of plastic, rubber, metal, or any other material that is known or useful in the art. Additionally, the fill port can comprise an opening in the rigid container 202 and a means to seal the opening. This means the fill port can be sealed using various means, including, but not limited to: glue, sealants, heat-sealing, solid plugs, etc. In various embodiments, the post filling seal is a hermetic seal.

In various embodiments, the vent can be positioned on a side opposite that of the fluid outlet. In this configuration, mixing liquid can enter the rigid container via the fluid inlet at the same time that air is evacuated through the vent. In various embodiments, the vent can be positioned so that it is positioned at the high point of the rigid container relative to the fluid inlet and/or the fluid outlet in order to maximize air evacuation during filling. In various embodiments, vent can be configured to allow for only air to evacuate while retaining all the liquid within the rigid container 202.

In various embodiments, media mixing system 200 can further comprise a fluid supply line 204 that can be fluidically connected to the fluid inlet of the rigid container 202 and configured to supply a mixing fluid to the container 202. In various embodiments, a fluid dispensing line 206 can be fluidically connected to the fluid outlet of the rigid container 202 and configured to dispense solubilized media from the rigid container 202. In various embodiments, a filter element 210 can be fluidically connected to the fluid dispensing line 206 and be configured to sterilize solubilized media dispensed from the rigid container 202.

In various embodiments of media mixing system 200, the rigid container 202 (with or without the flexible portion 102) can have a volumetric capacity ranging from about 1 to about 50 liters. In various embodiments, the rigid container 202 can have a volumetric capacity ranging from about 15 liters to about 30 liters. However, those skilled in the art will appreciate that a rigid container 202 can come in any size as long as it can function to either provide lateral or structural support for the flexible portion 102 that it contains or can maintain structural integrity during a media rehydration operation (in the case of where the rigid container 202 functions without a flexible portion 102).

It should be understood that the media mixing system 200 can also include one or more components and/or subsystems that allow an operator to control the pH, $dO_2$ concentration and/or temperature of media that is rehydrated in the rigid container 202 (with or without the flexible portion 102). That is, the rigid container 202 and/or flexible portion 102 can also include sensors and other devices. In various embodiments, the flexible portion 102 includes a pH sensor and dissolved-oxygen sensor. As such, the sensors are disposed partly or entirely in the flexible portion 102. In various embodiments, the sensors are attachable to the flexible portion 102 and are separate units. Such sensors may optionally be reusable after sterilization. In various embodiments, the rigid container 202 includes a product loop with flow past a pH sensor and dissolved-oxygen sensor, wherein the sensors are incorporated into the rigid container 202 itself.

The system 200 is flexible and provides alternative ways of supplying optional equipment of various kinds (e.g., sensors, probes, devices, pouches, ports, etc.). The system 200 may also include one or more internal pouches that are sealed to the flexible portion 102. In various embodiments, the pouch has at least one end that can be opened to the outside of the flexible portion 102 to insert a probe into the flexible portion 102 while remaining on the exterior of the flexible portion 102. The probe may be, for example, a temperature probe, a pH probe, a dissolved gas sensor, an oxygen sensor, an osmometer or any other probe that allows for testing or checking the liquid media during or at the completion of the rehydration process.

FIGS. 3A-3D depict illustrations of the media mixing system 200 described above, in accordance with various embodiments. As depicted herein, the rigid container 202 of the media mixing system 200 further includes a transparent portion 302 that can allow an operator to view the flexible portion prior to and/or during the dry media rehydration process. This has certain advantages as it can allow the operator to detect defects (e.g., packaging defects, dry media loading errors, etc.) in the rigid container 202 or the flexible media vessel portion (e.g., bag, liner, etc.) packed into rigid container 202 prior to the start of the rehydration process and detect errors (e.g., leaks, media clumping, etc.)/monitor rehydration progress once the rehydration process starts. The fluid supply 204 and fluid dispensing 206 lines are directly connected to the flexible portion via an opening 304 at the base of the rigid container 202. An automatic valve 306 is fluidically connected to the fluid supply line 204 upstream from the flexible portion housed in the rigid container. A sensor element 308 is fluidically connected to the fluid dispensing line 206 upstream from a filter element 310. The automatic valve 306 is communicatively connected to the sensor element 308 and is configured to adjust the flow rate of the mixing fluid supplied to the rigid container 202 or the flexible portion housed within rigid container 202 based on measurements of physicochemical properties of the solubilized media in fluid dispensing line 206 that are relevant to the rehydration of the dry media contained in the rigid container 202 or flexible portion. In various embodiments, the system 200 depicted in FIGS. 3A-D include a system control module that is in communications with both the automatic valve 306 and the sensor element 310. The system control module can be configured to generate instructions to adjust flow rate settings on automatic valve 306 in response to measurement data received from sensor element 310.

In various embodiments, the system 200 depicted in FIGS. 3A-D can further include a pressure regulator fluidically connected to the dispensing line 206 upstream from the filter element 310. The pressure regulator can be configured to variably reduce flow rate of the solubilized media dispensed from the fluid dispensing line 206 when the fluid pressure in the fluid dispensing line exceeds a predetermined setting.

FIGS. 4A-D depict illustrations of the media mixing system 200 described above, in accordance with various embodiments. As depicted herein, the rigid container 202 of the media mixing system 200 includes a manifold element 402 integrated into the rigid container 202. The manifold element 402 can be fluidically connected to the fluid supply 204 and fluid dispensing 206 lines on one side while being fluidically connected to the fluid inlet and fluid outlet ports of the flexible portion (i.e., pre-loaded media mixing vessel) housed in the rigid container 202 on the opposite side. An automatic valve 306 is fluidically connected to the fluid supply line 204 upstream from the manifold element 402. A sensor element 308 is fluidically connected to the fluid dispensing line 206 upstream from a filter element 310. The automatic valve 306 is communicatively connected to the sensor element 308 and is configured to adjust the flow rate of the mixing fluid supplied to the flexible portion housed within rigid container 202 based on measurements of physicochemical properties of the solubilized media in fluid dispensing line 206 that are relevant to the rehydration of the dry media contained in the flexible portion. In various embodiments, the system 200 depicted in FIGS. 4A-D can include a system control module that is in communication with both the automatic valve 306 and the sensor element 308. The system control module can be configured to generate instructions to adjust flow rate settings on automatic valve 306 in response to measurement data received from sensor element 310.

In various embodiments, the system 200 depicted in FIGS. 4A-D can further include a pressure regulator fluidically connected to the dispensing line 206 upstream from the filter element 310. The pressure regulator can be configured to variably reduce flow rate of the solubilized media dispensed form the fluid dispensing line 206 when the fluid pressure in the fluid dispensing line exceeds a predetermined setting.

FIGS. 5A-F, depict illustrations of the media mixing system 200 described above, in accordance with various embodiments. As depicted herein, an integrated media mixing system cart 502 includes an integrated rigid container 504 and upper 402(a) and lower 402(b) integrated manifold elements. The upper integrated manifold element 402(a) can be fluidically connected to one or more fluid dispensing lines 206 connecting one or more media mixing system carts 502 in series. Likewise, the lower integrated manifold element 402(b) can be fluidically connected to one or more fluid supply lines 204 to do the same.

An automatic valve (housed within integrated media mixing system cart 502) is fluidically connected to the fluid supply line 204 upstream from the lower integrated manifold element 402(b). A sensor element 308 is fluidically connected to the fluid dispensing line 206 upstream from a filter element 310. The automatic valve 306 is communicatively connected to the sensor element 308 and is configured to adjust the flow rate of the mixing fluid supplied to the flexible portion housed within rigid container 202 based on measurements of physicochemical properties of the solubilized media in fluid dispensing line 206 that are relevant to the rehydration of the dry media contained in the flexible portion. In various embodiments, the system 200 depicted in FIGS. 5A-F include a system control module (integrated within the integrated media mixing system cart 502) that is in communications with both the automatic valve 306 and the sensor element 308. The system control module can be configured to generate instructions to adjust flow rate settings on automatic valve 306 in response to measurement data received from sensor element 310. The system control module can be programmed by an operator through a user interface 506, such as a touch screen, provided on the integrated media mixing system cart 502. In various embodiments, the sensor element 308 and the filter element 310 are housed within the integrated media mixing system cart 502.

Figure 6A:
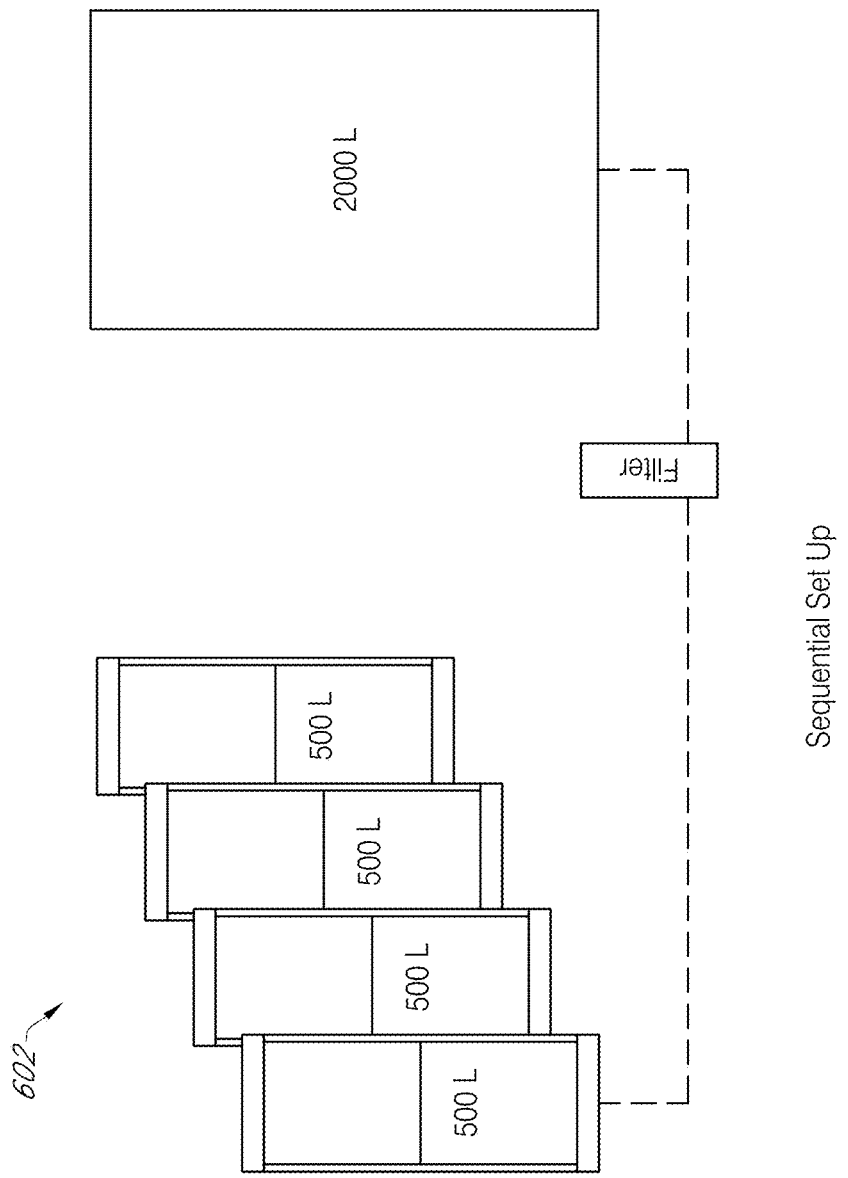
FIGS. 6 A-B are schematic diagrams of implementations of a scalable multi-container media rehydration system, in accordance with various embodiments.
Figure 6B:
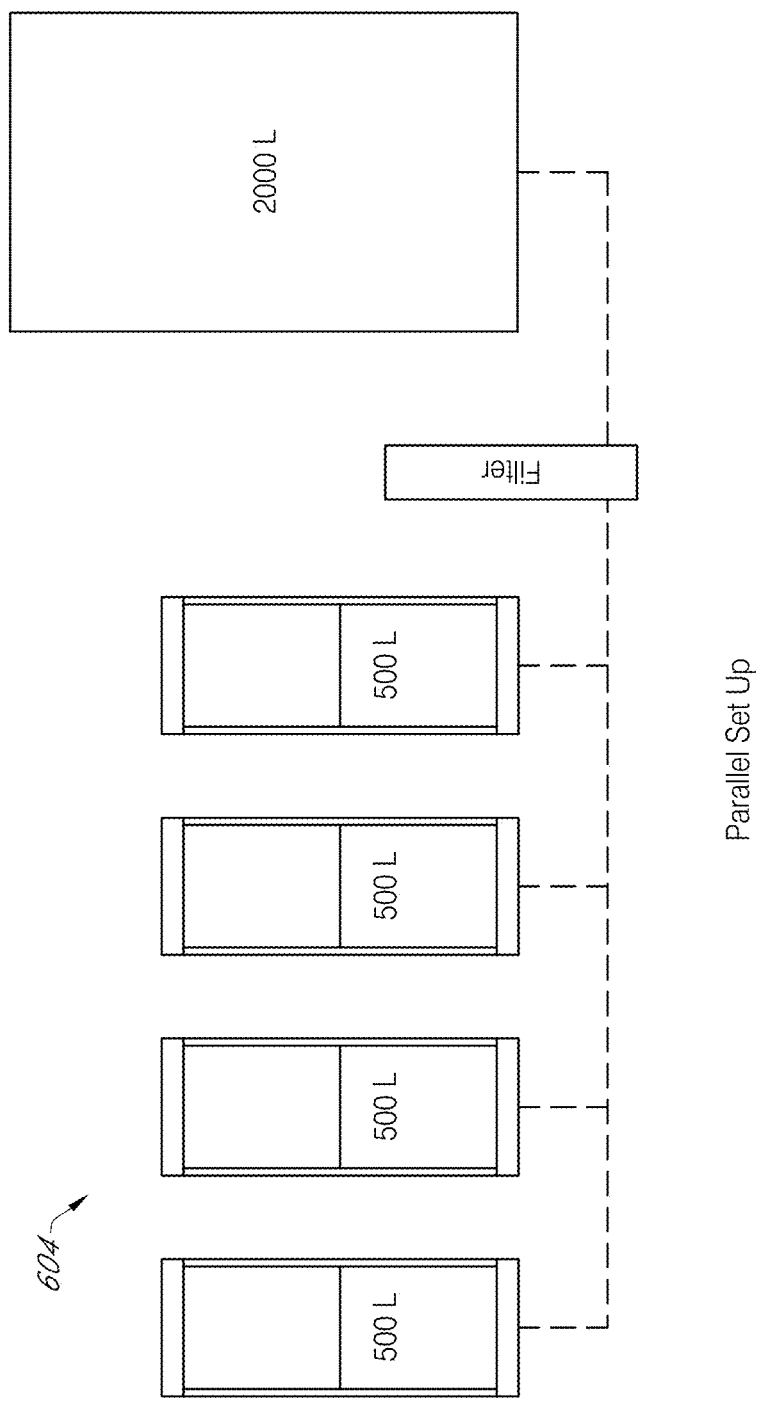

In various embodiments, the system 200 depicted in FIGS. 5A-F can further include a pressure regulator fluidically connected to the dispensing line 206 upstream from the filter element 310. The pressure regulator can be configured to variably reduce flow rate of the solubilized media dispensed form the fluid dispensing line 206 when the fluid pressure in the fluid dispensing line exceeds a predetermined setting. In various embodiments, the pressure regulator can be housed in the integrated media mixing system cart 502.
Scalable Media Mixing System with Multiple Media Mixing Containers The volume of media required varies significantly depending on the particular application. Small research laboratories may have low volume media requirements that necessitate only a single media mixing container (i.e., media mixing system 200). However, large commercial production facilities may require vast quantities of media that cannot be supplied by a single media mixing container. That is why various embodiments disclosed herein can make use of more than one media container described above. As shown in FIGS. 6A and 6B, these larger systems can use a manifold system to fluidically connect a plurality of media mixing containers either in parallel 602 or in series 604 to rehydrate dry media contained in more than one media mixing container at the same time. Through such a manifold system the volume of media production can theoretically be scaled up infinitely.

Figure 7A:
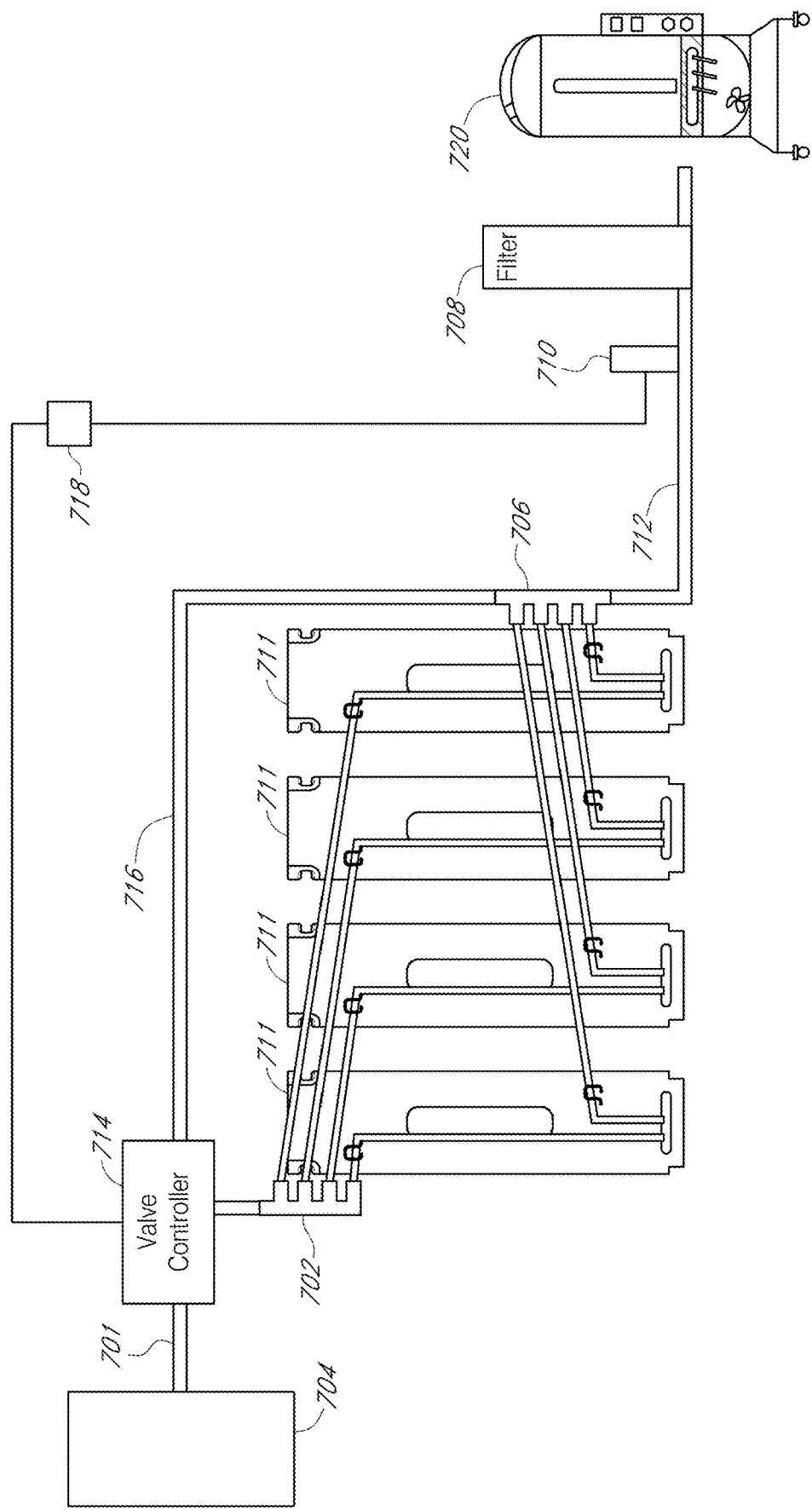
FIG. 7A is a schematic diagram of a scalable media mixing system, in accordance with various embodiments.

FIG. 7A is a schematic diagram of a scalable media mixing system, in accordance with various embodiments. As depicted herein, a scalable media mixing system 700 can include an inlet manifold 702, an outlet manifold 706, a fluid supply line valve 714, a sensor element 710, a main fluid supply line 701, a fluid dilution line 716, a consolidated fluid dispensing line 712 and two or more media mixing containers 711. The inlet manifold 702 is fluidically connected to the main fluid supply source 704 (via the main fluid supply line 701) and each of the media mixing containers 711 that comprise the scalable media mixing system 700. The fluid supply line valve 714 is fluidically connected to the main fluid supply line 701 (upstream from the inlet manifold 702) and the fluid dilution line 716. In various embodiments, the fluid supply line valve 714 is configured to function as time-delayed automated flow control valve (e.g., automated solenoid valve, etc.) that can adjust the flow rate of mixing fluid supplied to the main fluid supply line 701 and/or the fluid dilution line 716 according to one or more pre-defined time intervals. That is, the fluid supply line valve 714 can be programmed by an operator to increase or decrease the flow rates of mixing fluid supplied to the main fluid supply line 701 and/or the fluid dilution line 716 based on a number of different time points during the dry media rehydration process.

The outlet manifold 706 is fluidically connected to the consolidated fluid dispensing line 712, the fluid dilution line 716 and each of the media mixing containers 711 that comprise the scalable media mixing system 700. The consolidated fluid dispensing line 712 dispenses solubilized media discharged from each of the media mixing containers 711 connected to the system 700. In various embodiments, the fluid supply line valve 714 is configured to be manually operated by an operator to increase or decrease the flow rate of mixing fluid supplied to the main supply line 701 and/or the fluid dilution line 716 as required by the particular media rehydration process.

In various embodiments, each media mixing container 711 in the system 700 has a cavity with a first volumetric capacity and an inner wall configured to supply lateral support for a flexible media mixing vessel (i.e., flexible portion) housed in the container 711. In this configuration, each of the flexible media mixing vessels is fluidically connected to the inlet manifold 702 and the outlet manifold 706. In various embodiments, each flexible media mixing vessel can have a second volumetric capacity that can be larger than the first volumetric capacity of media mixing container 711. In various embodiments, the flexible media mixing vessels in the system can be configured to contain dry media. In various embodiments, each media mixing container 711 can be directly filled with dry media without the use of a flexible media mixing vessel. Ideally, the rigid container is comprised of materials that are not chemically reactive with the dry media, the media mixing fluids or the resultant liquid media from the media rehydration operation. That is, the rigid container materials do not leach or release residues into the rehydrated media after the media rehydration process is complete. In various embodiments, the rigid container can be pre-filled with dry media, thus eliminating the need for an operator to weigh and fill container with media prior to use.

In various embodiments, system 700 can include a filter element 708 that is fluidically connected to the consolidated fluid dispensing line 712 and is configured to sterilize solubilized media dispensed from the outlet manifold 706. In various embodiments, the filter element 708 can serve to ensure that particulates exceeding a certain size are not fed into the bioreactor 720.

In various embodiments, the sensor element 710 is fluidically connected to the consolidated fluid dispensing line 712 upstream or adjacent to the filter element 708. In various embodiments, the sensor element 710 is in direct communication with the fluid supply line valve 714 and is configured to provide various types of sensor measurements to the fluid supply line valve 714 in order to trigger its activation.

In various embodiments, the sensor element 710 is a pressure transducer configured to measure fluid pressure of the consolidated fluid dispensing line 712 and generate communication signals (either electrically or mechanically) that can activate the fluid supply line valve 714 to open or close, thereby, increasing or decreasing the flow rate of mixing fluid supplied to the main fluid supply line 701 and/or the fluid dilution line 716.

In various embodiments, the sensor element 710 is a conductivity sensor configured to measure the fluid conductivity of the solubilized media in the consolidated fluid dispensing line 712 and communicate those measurements back to the fluid supply line valve 714 to increase or decrease the flow rate of mixing fluid supplied to the main fluid supply line 701 and/or the fluid dilution line 716. In various embodiments, the sensor element 710 is an optical sensor configured to measure a concentration of the solubilized media in the consolidated fluid dispensing line 712 and communicate those measurements back to the fluid supply line valve 714 to increase or decrease the flow rate of mixing fluid supplied to the main fluid supply line 701 and/or the fluid dilution line 716.

In various embodiments, the system 700 includes a system control component 718 that is communicatively connected to fluid supply line valve 714. In various embodiments, the system control component 718 can be configured to provide instructions to increase or decrease the flow rates of mixing fluid supplied to the main fluid supply line 701 and/or the fluid dilution line 716 based on one or more pre-defined time intervals or time point settings.

In various embodiments, system 700 can also include a system control component 718 that can be configured to receive information from the sensor element 710 and then send a signal to activate the fluid supply line valve 714 to increase or decrease the flow rate of mixing fluid supplied to the main fluid supply line 701 and/or the fluid dilution line 716. In various embodiments, the signal strength can determine to what degree the fluid supply line valve 714 increases or decreases the flow rates of the mixing fluids supplied to the main fluid supply line 701 and/or the fluid dilution line 716. In various embodiments, one or more flexible portions can be housed simultaneously in each of the media mixing containers 711 allowing for hydration of dry media contained in several flexible media mixing vessels at the same time in the same container 711. In various embodiments, the inlet manifold 402 can be directly connected to the flexible media mixing vessel. In various embodiments, the flexible media mixing vessel can be connected to a first adapter and the inlet manifold 702 can be connected to a second adapter that is in fluid communication with the first adapter.

In various embodiments, the outlet manifold 706 can be directly connected to the flexible media mixing vessel. In various embodiments, the flexible media mixing vessel can be connected to a first adapter and the outlet manifold 706 can be connected to a second adapter that is in fluid communication with the first adapter.

In various embodiments, the media mixing containers 711 are oriented such that the vent, such as a gas bleed valve or microporous hydrophobic membrane, on the flexible media mixing vessel is set at a position that is elevated relative to the fluid outlet on the mixing vessel. The vent can be configured to allow for only air to evacuate while retaining all liquid.

Figure 7B:
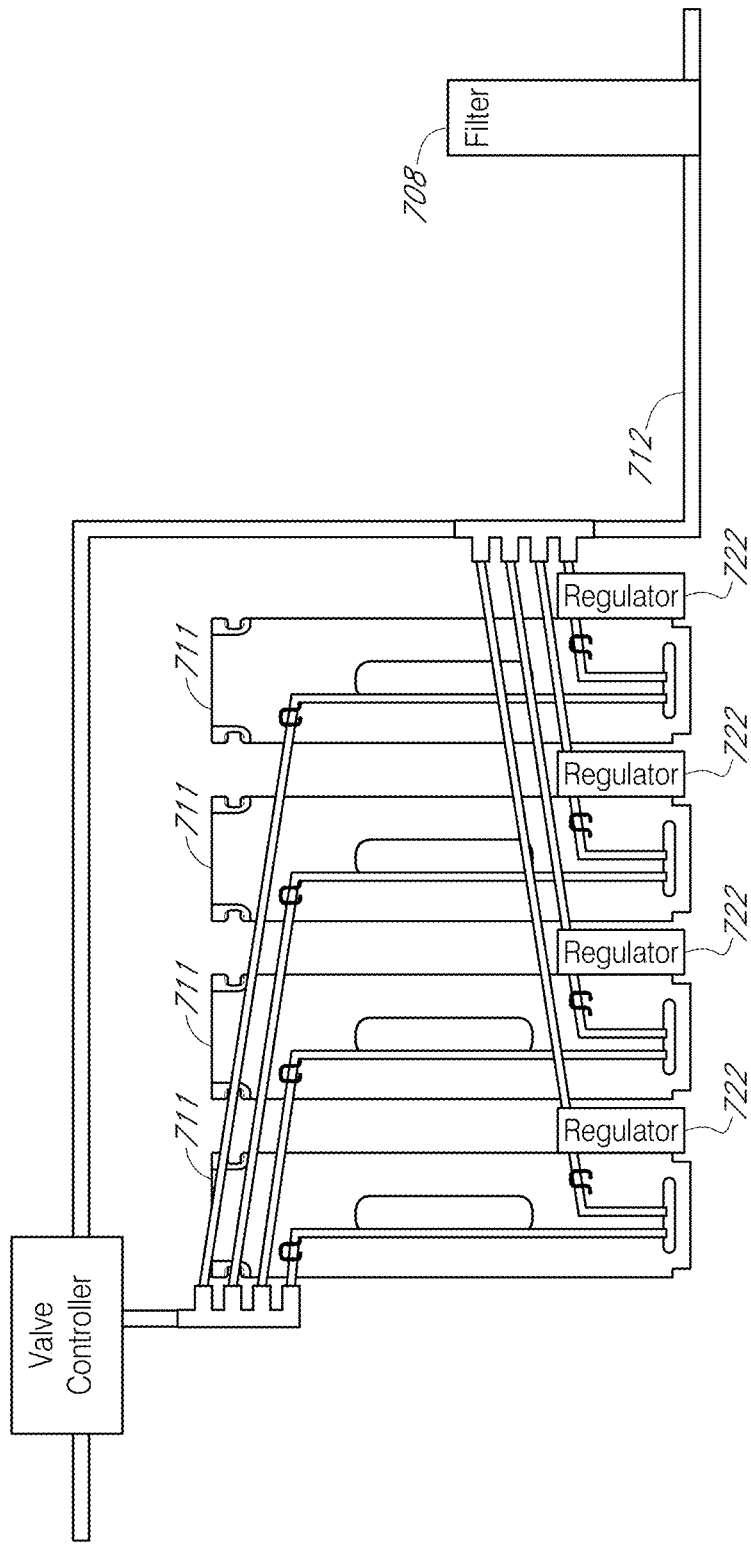
FIG. 7B is a schematic diagram of a scalable media mixing system with external fluid dispensing line pressure regulators, in accordance with various embodiments.
Figure 7C:
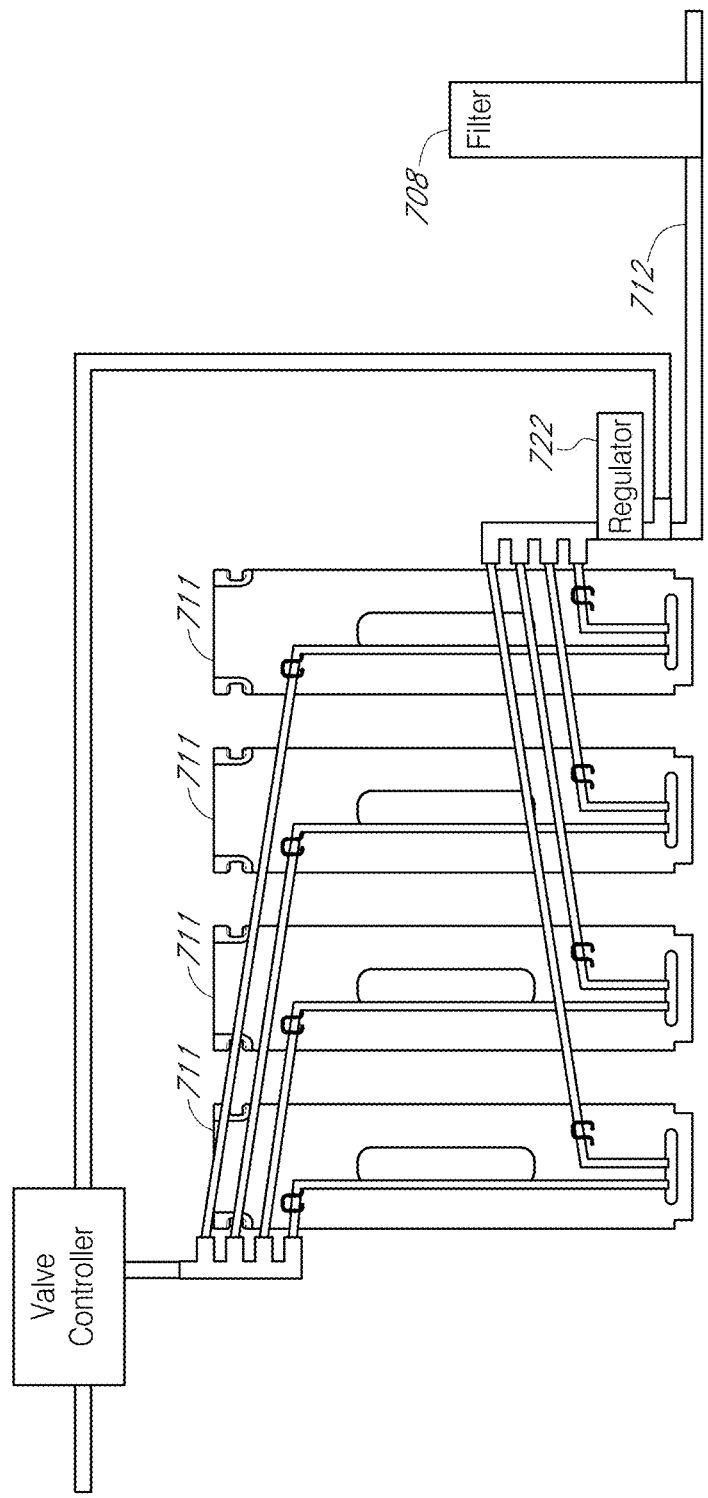
FIG. 7C, is a schematic diagram of a scalable media mixing system with an external main pressure regulator downstream from the outlet manifold, in accordance with various embodiments.

In various embodiments, the flexible media mixing vessel is pre-packaged with dry media prior to being shipped to a customer. The dry media can be AGT, DPM, or any other dry media format that can be effectively rehydrated by this system 700. In various embodiments, system 700 can include one or more pressure regulators placed upstream of filter element 708. The pressure regulators can be configured to variably reduce flow rate of the solubilized media dispensed from the fluid dispensing lines when the fluid pressure in the fluid dispensing line exceeds a predetermined setting. The purpose of these regulators is to prevent the filter element 708 from being clogged by unsolubilized media particles as any clogging of the filter element 708 will result in an increase in fluid pressure within the fluid dispensing line. In various embodiments, as depicted in FIG. 7B, the pressure regulator 722 can be fluidically connected to the fluid dispensing line outside of each media mixing container 711. In various embodiments, as depicted in FIG.

Figure 7D:
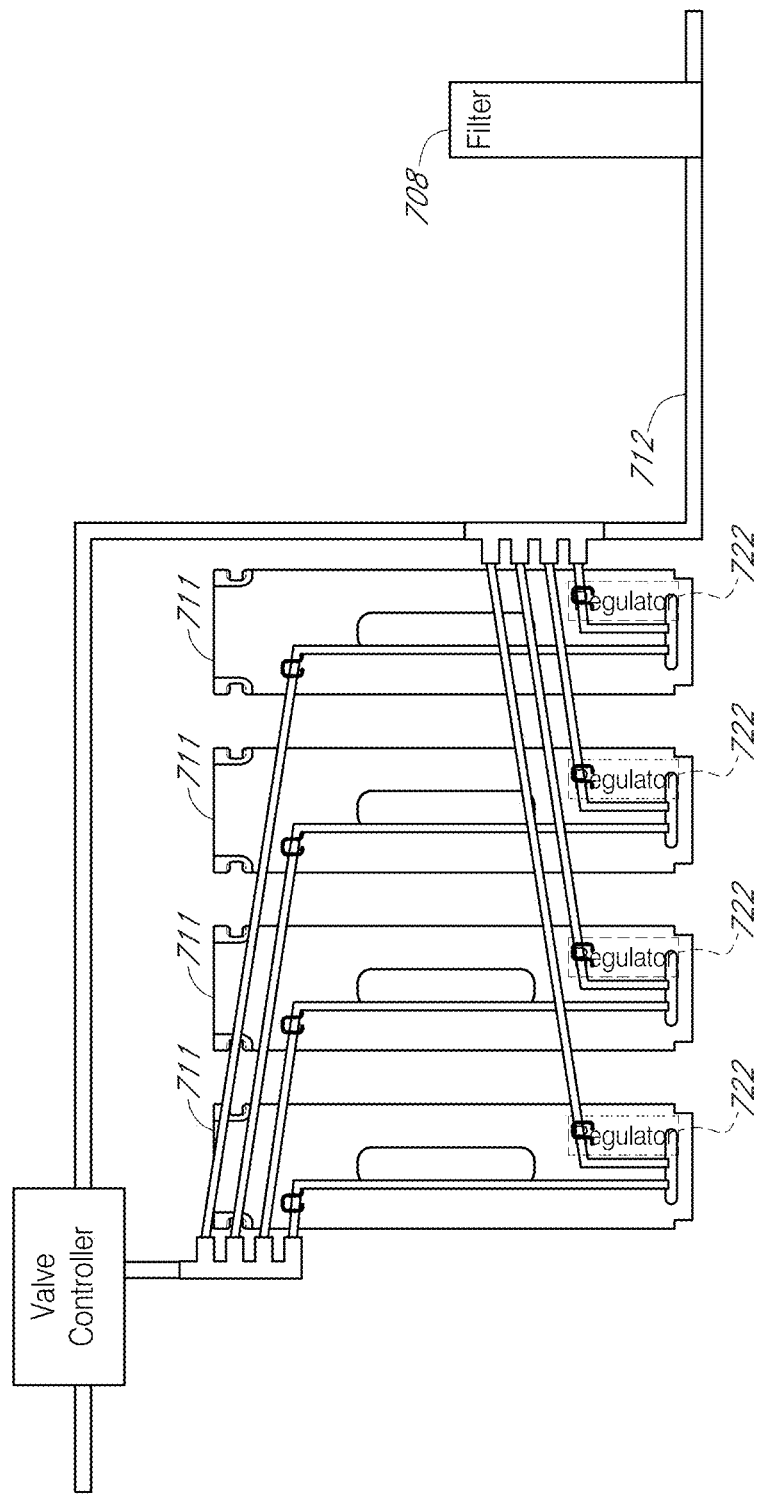
FIG. 7D is a schematic diagram of a scalable media mixing system with internal fluid dispensing line pressure regulators, in accordance with various embodiments.

7C, the pressure regulator 722 can be fluidically connected to the consolidated media dispensing line 712 upstream from the filter element 708. In various embodiments, as depicted in FIG. 7D, the pressure regulator 722 can be fluidically connected to the media dispensing line of each media mixing container 711 and housed in the media mixing container 711.

Figure 8:
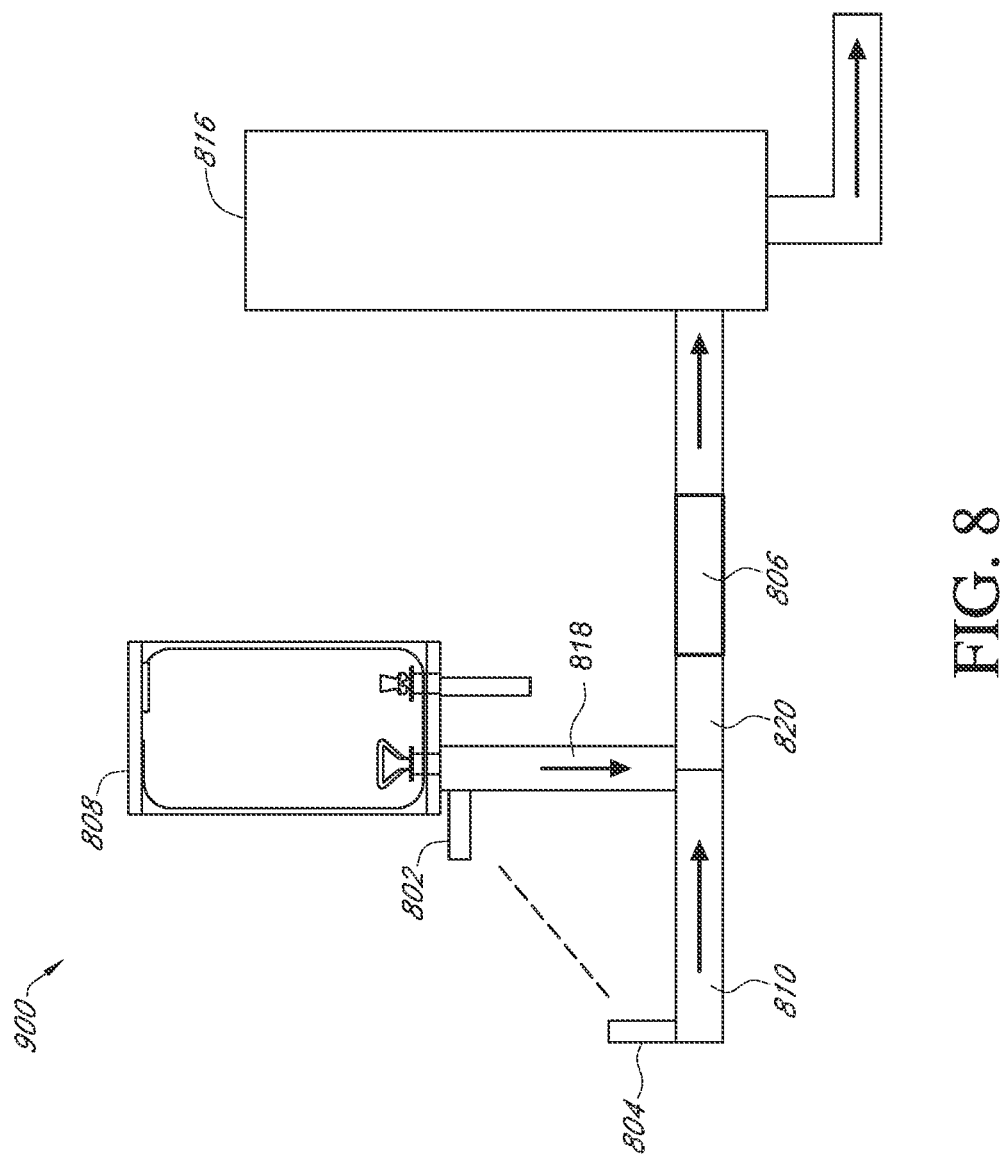
FIG. 8 is a schematic diagram of a media mixing container system, in accordance with various embodiments.

FIG. 8 is a schematic diagram of a scalable media mixing system, in accordance with various embodiments. As depicted herein, a scalable media mixing system 800 can include a media mixing container 808, a fluid outlet line 818, a fluid dilution line 810, a fluid dispensing line 820, a back pressure monitor 802, a control valve 804, a pre-filter element 806, and a filter element 816. The media mixing container 808 is fluidically connected to the fluid outlet 818. The fluid dilution line 810 and the fluid outlet line 818 are fluidically connected to the fluid dispensing line 820 and the fluid dispensing line 820 is downstream from the media mixing container 808. In various embodiments, the back pressure monitor 802 is configured to read a back pressure in the fluid outlet line 818. In various embodiments, the control valve 804 is configured to adjust the flow rate of fluid in the fluid dilution line 810. In various embodiments, the back pressure monitor 802 is in communication with the control valve 804 and the control valve 804 can open or close based on the back pressure.

In various embodiments, there is more than one fluid outlet line 818 and they converge into a fluid outlet manifold. The back pressure monitor 802 can be connected to the fluid outlet line 818 and/or the fluid outlet manifold and can be configured to monitor the back pressure in either the fluid outlet line 818 and/or the fluid outlet manifold. In various embodiments, the back pressure monitor 802 can be located anywhere upstream of the fluid dispensing line 820.

In various embodiments, the pre-filter element 806 is fluidically connected to the fluid dispensing line 820 and can comprise a static mixer, coil, tube, secondary tank, in-line mixer, spiral mixer, pump, or filter and can be configured to ensure adequate mixing and dissolution of diluted media. In the various embodiments where the pre-filter element comprises a mixer, the mixer can further comprise paddles, propellers, magnetic stirrers, bubble generators, or any combination thereof. In various embodiments, the pre-filter element 806 can be located before the filter element 816. In the various embodiments where the pre-filter element 806 comprises a filter, the filter can further comprise pores of about 0.45 microns in size. In various embodiments the filter can comprise pores of about 0.40 microns to about 0.50 microns in size. In various embodiments the filter can comprise pores of about 0.35 microns to about 0.55 microns in size.

Methods for Media Rehydration

Figure 9:
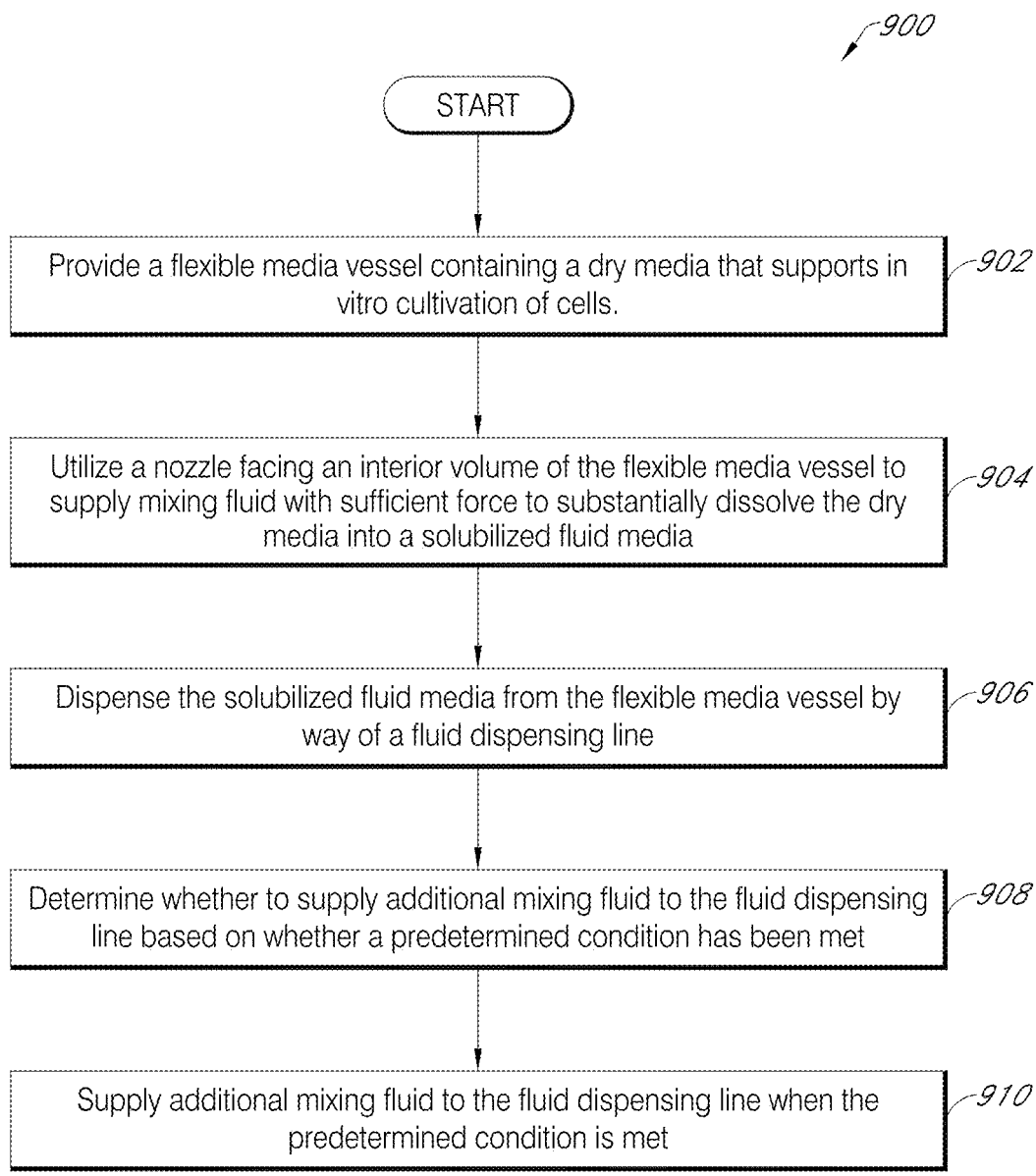
FIG. 9 is an exemplary flowchart showing a method 900 for rehydrating media, in accordance with various embodiments.

FIG. 9 is an exemplary flowchart showing a method 900 for rehydrating media, in accordance with various embodiments.

In step 902, a media vessel containing a dry media that supports in vitro cultivation of cells is provided. In various embodiments the dry media can be comprised of particles of about 150 to about 15,000 microns in size. In various embodiments the media can be comprised of particles of about 300 to about 15,000 microns in size. In various embodiments the media can be comprised of particles of about 150 to about 300 microns in size. The granular size of the individual media particles can be determined by the dry media type (e.g., AGT, DPM, etc.), particular application or the ingredients that the dry media is comprised of. In various embodiments, the media vessel can be a flexible containment device such as a bag or a liner. In various embodiments, the media vessel can be a rigid container, such as the one described above.

In step 904, a nozzle facing an interior volume of the media vessel is used to supply mixing fluid with sufficient force to substantially dissolve (effectively mix) the dry media into a solubilized fluid media.

In various embodiments the nozzle can be comprised of an eductor or equivalent device designed to entrain (i.e., recirculate) liquid in the media vessel as motive (supply) liquid moves through the nozzle. In various embodiments, the nozzle can be configured to produce an entrainment ratio (i.e., volume of recirculating fluid to motive or supply fluid) of at least about 5 parts recirculating fluid to about 1 part motive fluid. This ratio can change depending on the type of dry media that is being rehydrated and/or the specific application. For example, the circulation ratio can be 1:1, 2:1, 3:1, 4:1, 5:1, or any other ratio that is available and useful depending on the particular application.

In various embodiments, the nozzle has an orifice diameter that can directly impact the velocity of mixing fluid that flows through the nozzle into the media vessel at any given fluid supply flow rate. That is, mixing fluid velocity through the nozzle is equal to the flow rate divided by the orifice area (as determined from the orifice diameter). The nozzle's orifice diameter can depend on a variety of factors including, but not limited to, the specific application that the media vessel is being used for, the size of the media vessel, fluid supply pressure, fluid supply flow rate, etc.

In various embodiments, the nozzle orifice has a diameter of between about 1.0 millimeters (mm) to about 10 mm. In various embodiments, the nozzle orifice has a diameter of between about 3.0 mm to about 6.0 mm. In various embodiments, the nozzle orifice has a diameter of between about 6.0 mm to about 10.0 mm.

In various embodiments, a nozzle with an orifice diameter of between about 1.0 mm to about 10 mm is configured to supply fluid to the media vessel with a flow power of at least 10 Watts (W). In various embodiments, a nozzle with an orifice diameter of between 3 mm to about 6 mm is configured to supply fluid to the media vessel with a flow power of at least 15 W. In various embodiments, a nozzle with an orifice diameter of between about 6 mm to about 10 mm is configured to supply fluid to the media vessel with a flow power of at least 10 W. In various embodiments, a nozzle with an orifice diameter of between about 1.0 mm to about 10 mm is configured to supply fluid to the media vessel with an average mixing velocity of between about 7 meters per second (m/s) to about 19 m/s. In various embodiments, a nozzle with an orifice diameter of between 3 mm to about 6 mm is configured to supply fluid to the media vessel with an average mixing velocity of between about 14 m/s to about 19 m/s. In various embodiments, a nozzle with an orifice diameter of between about 6 mm to about 10 mm is configured to supply fluid to the media vessel with an average mixing velocity of between about 7 m/s to about 14 m/s.

In various embodiments, a nozzle with an orifice diameter of between about 1.0 mm to about 10 mm is supplied with mixing fluid at a rate of between about 1 liter per minute (LPM) to about 75 LPM. In various embodiments, a nozzle with an orifice diameter of between 3 mm to about 6 mm is supplied with mixing fluid at a rate of between about 5 LPM to about 35 LPM. In various embodiments, a nozzle with an orifice diameter of between about 6 mm to about 10 mm is supplied with mixing fluid at a rate of between about 5 LPM to about 35 LPM.

In various embodiments, a nozzle with an orifice diameter of between about 1.0 mm to about 10 mm is supplied with mixing fluid at a fluid pressure of between about 1 pound per square inch (psi) to about 60 psi. In various embodiments, a nozzle with an orifice diameter of between 3 mm to about 6 mm is supplied with mixing fluid at a fluid pressure of between about 10 psi to about 40 psi. In various embodiments, a nozzle with an orifice diameter of between about 6 mm to about 10 mm is supplied with mixing fluid at a fluid pressure of between about 5 psi to about 15 psi.

In step 906, the solubilized fluid media is dispensed from the media vessel by way of a fluid dispensing line. In various embodiments, a pressure regulator is fluidically connected to the fluid dispensing line and configured to variably reduce flow rate of the solubilized media dispensed from the fluid dispensing line when the fluid pressure in the fluid dispensing line exceeds a predetermined setting.

In step 908, a determination is made on whether to supply additional mixing fluid to the fluid dispensing line based on whether a predetermined condition has been met. In various embodiments, the predetermined condition is based on sensor measurements of the physicochemical properties of the solubilized media in the fluid dispensing line that are relevant to the rehydration of the dry media contained in the media vessel. Examples of relevant physicochemical properties include, but are not limited to, fluid pressure in the fluid dispensing line, electrical conductivity of the solubilized media, concentration of the solubilized media, etc. In various embodiments, the determination is made by an automatic valve that is fluidically connected to the fluid supply line and communicatively connected to the sensor. In various embodiments, the determination is made by a system control module that is communicatively connected to the sensor.

In step 910, additional mixing fluid is supplied to the fluid dispensing line when the predetermined condition is met. In various embodiments, a fluid dilution line is fluidically connected to the fluid dispensing line and configured to supply mixing fluids to further dilute the solubilized media in the fluid dispensing line. In various embodiments, an automatic valve that is fluidically connected to the fluid dilution line is configured to increase or decrease the flow rate of mixing fluids supplied by the fluid dilution line based on whether the predetermined condition has been met.

In various embodiments, a system control module that is in communications with both the automatic valve and the sensor is configured to generate instructions to adjust flow rate settings on the automatic valve in response to measurement data received from sensor.

Experimental Results

An eductor (or mixing nozzle as referenced above) forces incoming water through a restriction to create a high velocity jet which pulls additional water through a recirculation geometry due to a Bernoulli effect, inducing significant mixing. Velocity of water flowing through the eductor orifice is proportional to the flow rate divided by the orifice's area, and total flow power is proportional to the pressure drop across the eductor and the flow rate. A minimum velocity and power are required for an eductor to create effective mixing in the media rehydration systems, apparatuses and methods disclosed above. Thus, in sizing an eductor, the feed stream's flow rate/pressure capabilities should be taken into account, and an eductor should be selected such that the orifice area is small enough to achieve minimum effective velocity within the acceptable flow rate, but large enough to achieve minimum effective flow power within the acceptable pressure drop. To help identify the proper size eductor for use with the media rehydration systems, apparatuses and methods disclosed herein, several candidate eductors were experimentally assessed with respect to their mixing performance (e.g., orifice velocity, flow power, etc.) and pressure drops at different flow rates. The experiments utilized a water bath to mimic the capsule design with sand as a visual reference for mixing performance.

The following examples are offered to illustrate but not to limit the embodiments disclosed herein.

Example 1

Plot of Eductor Pressure for Different Orifice Sizes

Figure 10:
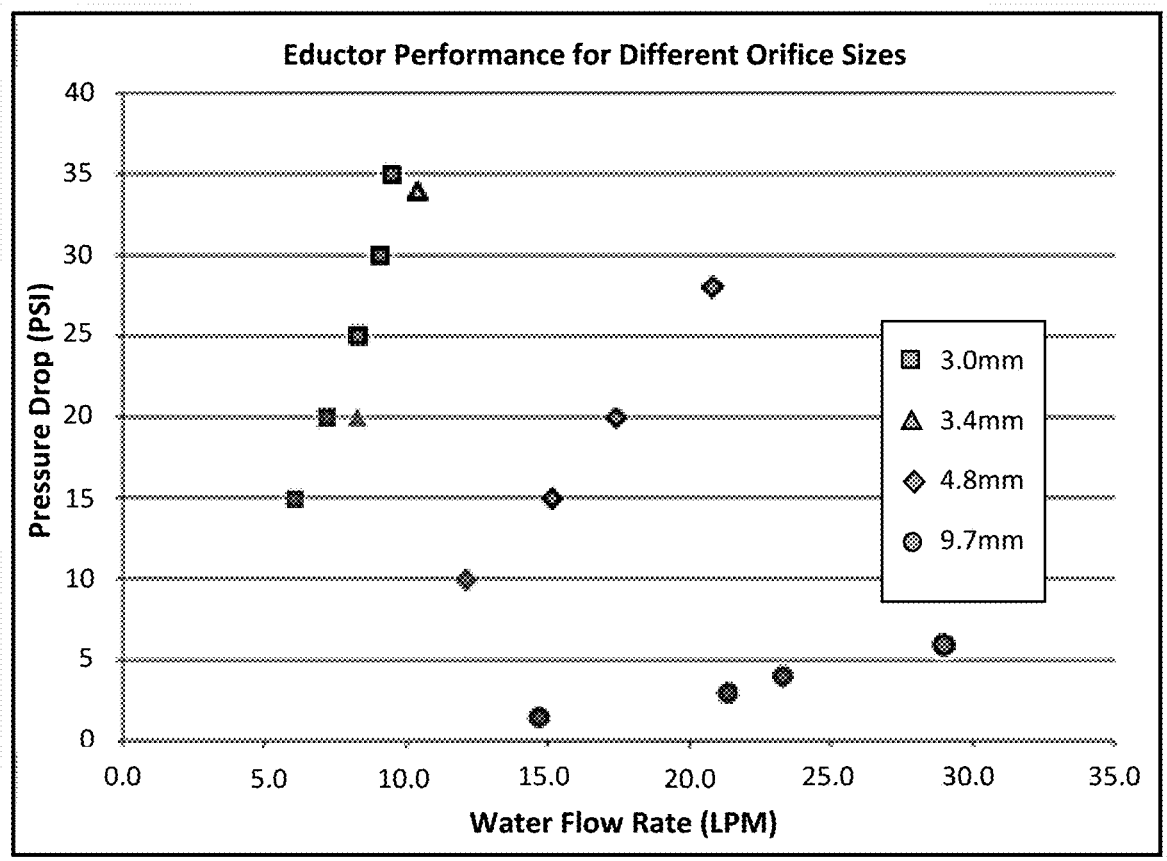
FIG. 10 is a graph plotting eductor pressure for different orifice sizes, in accordance with various embodiments.
Figure 11:
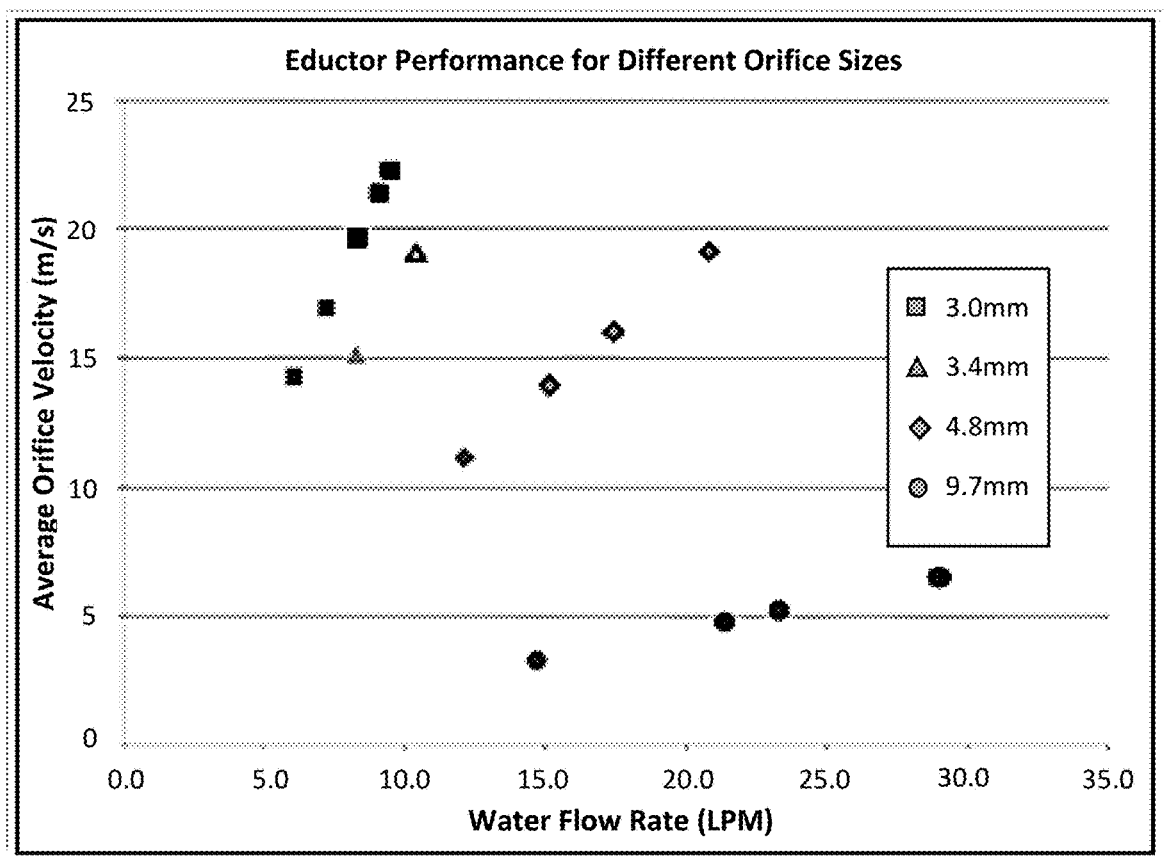
FIG. 11 is a graph plotting average eductor orifice velocity for different orifice sizes, in accordance with various embodiments.

Table 2 below and FIG. 10 summarize the mixing pressure, flow, and mixing performance of the eductors tested. As used herein, when "Mixing Effectiveness" is termed "Effective" it denotes a determination that the particular combination of eductor orifice diameter, inlet pressure and flow rate operational parameters resulted in effective mixing performance in the media rehydration systems, apparatuses and methods disclosed above.

TABLE 2

Eductor (Pressure Drop) Orifice Sizing Table

| Flow | Pressure Drop (PSIG) for Each Eductor Orifice Diameter | | | | Mixing |
|---|---|---|---|---|---|
| (LPM) | 4.8 mm | 3.0 mm | 3.4 mm | 9.7 mm | Effectiveness |
| 20.8 | 28 | | | | Effective |
| 17.4 | 20 | | | | Effective |
| 12.1 | 10 | | | | Ineffective |
| 15.1 | 15 | | | | Effective |
| 7.2 | | 20 | | | Ineffective |
| 6.1 | | 15 | | | Ineffective |
| 8.3 | | 25 | | | Effective |
| 9.1 | | 30 | | | Effective |
| 9.5 | | 35 | | | Effective |
| 8.3 | | | 20 | | Ineffective |
| 10.4 | | | 34 | | Effective |
| 14.7 | | | | 1.5 | Ineffective |
| 21.3 | | | | 3 | Ineffective |
| 23.3 | | | | 4 | Ineffective |
| 29.0 | | | | 6 | Effective |

Example 2

Plot of Average Eductor Orifice Velocity for
Different Orifice Sizes

Figure 12:
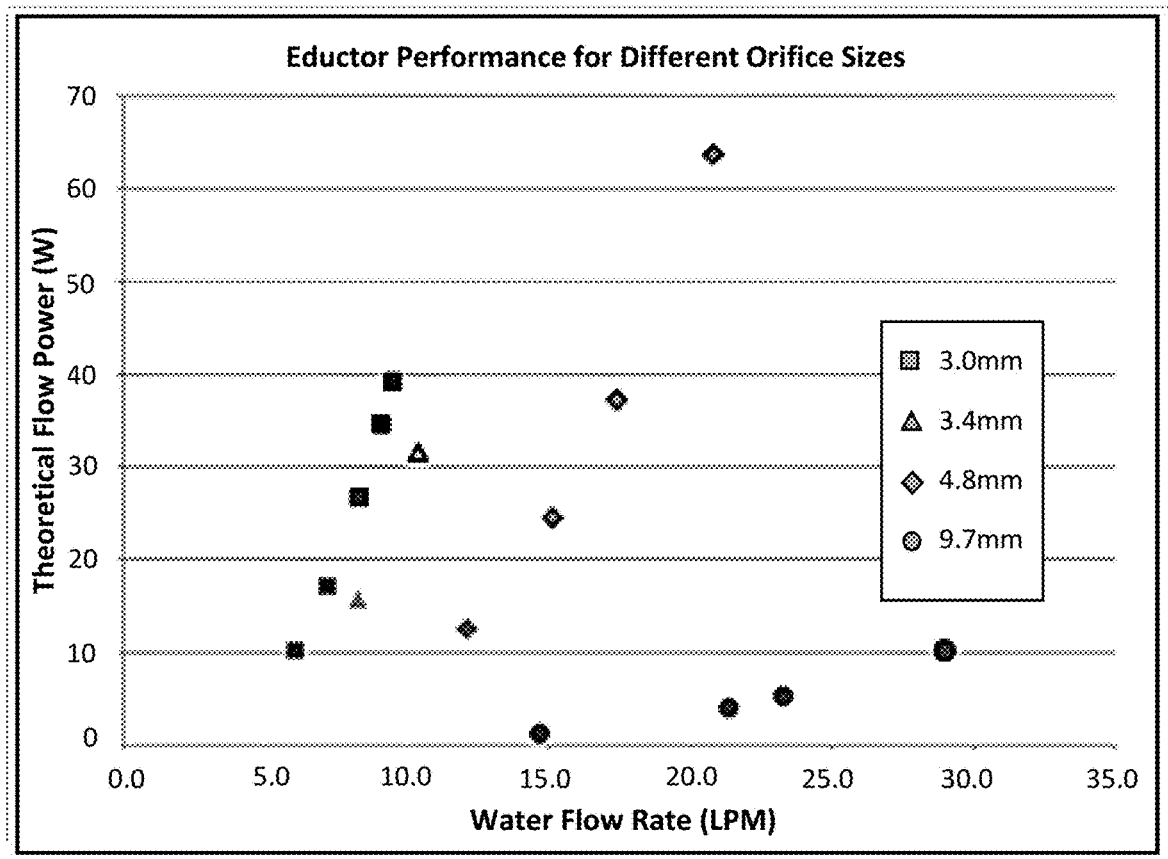
FIG. 12 is a graph plotting theoretical eductor flow power for different orifice sizes, in accordance with various embodiments.

As disclosed above, the average orifice velocity is equal to the flow rate divided by the orifice area. Orifice velocities for these experiments were calculated and summarized in the following Table 3 and FIG. 12, with black outlined data points on the graph again indicating effective mixing systems, apparatuses and methods disclosed above.

TABLE 3

Eductor (Average Orifice Velocity) Orifice Sizing Table

| Flow | Average Orifice Velocity (m/s) for Each Eductor Orifice Diameter | | | | Mixing |
|---|---|---|---|---|---|
| (LPM) | 4.8 mm | 3.0 mm | 3.4 mm | 9.7 mm | Effectiveness |
| 20.8 | 19 | | | | Effective |
| 17.4 | 16 | | | | Effective |
| 12.1 | 11 | | | | Ineffective |
| 15.1 | 14 | | | | Effective |
| 7.2 | | 17 | | | Ineffective |
| 6.1 | | 14 | | | Ineffective |
| 8.3 | | 20 | | | Effective |
| 9.1 | | 21 | | | Effective |
| 9.5 | | 22 | | | Effective |
| 8.3 | | | 15 | | Ineffective |
| 10.4 | | | 19 | | Effective |
| 14.7 | | | | 3 | Ineffective |
| 21.3 | | | | 5 | Ineffective |
| 23.3 | | | | 5 | Ineffective |
| 29.0 | | | | 7 | Effective |

Example 3

Plot of Theoretical Eductor Flow Power for
Different Orifice Sizes

As disclosed above, flow power is equal to one-half the mass flow rate times flow velocity squared. Theoretical flow powers for these experiments were calculated and summarize in the following Table 4 and FIG. 12, with black outlined data points on the graph again indicating effective mixing in the media rehydration systems, apparatuses and methods disclosed above.

TABLE 4

Eductor (Flow Power) Orifice Sizing Table

| Flow | Theoretical Eductor Power (W) for Each Eductor Orifice Diameter | | | | Mixing |
|---|---|---|---|---|---|
| (LPM) | 4.8 mm | 3.0 mm | 3.4 mm | 9.7 mm | Effectiveness |
| 20.8 | 64 | | | | Effective |
| 17.4 | 37 | | | | Effective |
| 12.1 | 13 | | | | Ineffective |
| 15.1 | 25 | | | | Effective |
| 7.2 | | 17 | | | Ineffective |
| 6.1 | | 10 | | | Ineffective |
| 8.3 | | 27 | | | Effective |
| 9.1 | | 35 | | | Effective |
| 9.5 | | 39 | | | Effective |
| 8.3 | | | 16 | | Ineffective |
| 10.4 | | | 32 | | Effective |
| 14.7 | | | | 1 | Ineffective |
| 21.3 | | | | 4 | Ineffective |
| 23.3 | | | | 5 | Ineffective |
| 29.0 | | | | 10 | Effective |

While the present teachings are described in conjunction with various embodiments, it is not intended that the present teachings be limited to such embodiments. On the contrary, the present teachings encompass various alternatives, modifications, and equivalents, as will be appreciated by those of skill in the art.

The invention claimed is:

1. A media mixing system, comprising:
a rigid container having a container cavity with a first volumetric capacity and a flexible media vessel with a second volumetric capacity that is smaller than the first volumetric capacity, the rigid container having an inner wall providing lateral support for the flexible media vessel, the flexible media vessel having an interior volume containing dry media;
a fluid supply line fluidically connected to an eductor coupled to the flexible media vessel and configured to supply a mixing liquid to the flexible media vessel, wherein the eductor is structurally designed such that during use as the mixing liquid is supplied to the interior volume of the flexible media vessel through the eductor, at least a portion of the supplied mixing liquid within the interior volume is re-entrained in the eductor, wherein during use the mixing liquid combines with the dry media to form a liquid media;

a fluid dispensing line fluidically connected to the flexible media vessel at a dispensing point and configured to dispense the liquid media from the flexible media vessel;

a filter fluidically connected to the fluid dispensing line downstream from the dispensing point and outside of the flexible media vessel; and a fluid dilution line fluidically connected to the fluid dispensing line at a location between the dispensing point and the filter so that the location is downstream of the dispending point and outside of the flexible media vessel, said fluid dilution line configured to supply additional mixing liquid to further dilute the liquid media in the fluid dispensing line after the liquid media is dispensed from the flexible media vessel.

2. The media mixing system of claim 1, wherein the fluid supply line is connected to flexible media vessel by way of a fluid inlet which includes the eductor disposed within the interior volume of the flexible media vessel.

3. The media mixing system of claim 2, wherein the eductor has an orifice diameter of between about 1 mm to about 10 mm.

4. The media mixing system of claim 2, wherein the eductor has an orifice diameter of between about 3 mm to about 6 mm.

5. The media mixing system of claim 2, wherein the eductor has an orifice diameter of between about 6 mm to about 10 mm.

6. The media mixing system of claim 3, wherein the eductor is configured to supply the mixing liquid into the flexible media vessel with a flow power of at least 10 w.

7. The media mixing system of claim 1, further comprising:

a sensor provided adjacent to or upstream from the filter element; and a fluid dilution control valve configured to increase or decrease a flow rate of the additional mixing liquid in the fluid dilution line in response to measurements provided by the sensor.

8. The media mixing system of claim 7, wherein the sensor comprises a pressure transducer configured to measure fluid pressure of the liquid media and activate the fluid dilution flow control valve to open or close to increase or decrease the flow rate of the additional mixing fluid supplied to the fluid dilution line.

9. A media mixing vessel, comprising:

a flexible portion having an interior volume, the interior volume containing dry media that supports in vitro cultivation of a cell;

a fluid inlet fluidically coupled to the flexible portion, wherein the fluid inlet includes an eductor positioned entirely within an interior volume of the flexible portion and configured to supply a mixing liquid to the interior volume as a motive liquid to dissolve the dry media, wherein the eductor is structurally designed to re-entrain the mixing liquid supplied to the interior volume of the flexible portion and the mixing liquid includes water or buffer that combines with the dry media to form a liquid media; and a fluid outlet fluidically coupled to the flexible portion, wherein the fluid outlet includes a filter element configured to prevent the dry media exceeding a predetermined size from exiting the flexible portion;

wherein the fluid inlet and the fluid outlet are not fluidically coupled to one another outside of the flexible portion;

wherein the eductor is the only mixing or agitating device within the interior volume of the flexible portion;

a vent operably coupled to the flexible portion and configured to evacuate air from the flexible portion; and a fill port operably coupled to the flexible portion and configured to hermetically seal after the flexible portion is filled with the dry media;

wherein the eductor is configured to supply the mixing liquid to dissolve the dry media in a single pass.

* * * * *